(12) United States Patent
Hollis

(10) Patent No.: US 11,864,753 B2
(45) Date of Patent: Jan. 9, 2024

(54) IMPLANT INSERTER

(71) Applicant: CROSSROADS EXTREMITY SYSTEMS, LLC, Memphis, TN (US)

(72) Inventor: M. Chad Hollis, Collierville, TN (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 688 days.

(21) Appl. No.: 16/483,409

(22) PCT Filed: Feb. 2, 2018

(86) PCT No.: PCT/US2018/016994
§ 371 (c)(1),
(2) Date: Aug. 2, 2019

(87) PCT Pub. No.: WO2018/145064
PCT Pub. Date: Aug. 9, 2018

(65) Prior Publication Data
US 2020/0008807 A1 Jan. 9, 2020

Related U.S. Application Data

(60) Provisional application No. 62/455,361, filed on Feb. 6, 2017.

(51) Int. Cl.
*A61B 17/064* (2006.01)
*A61B 17/068* (2006.01)
(Continued)

(52) U.S. Cl.
CPC ........ *A61B 17/0642* (2013.01); *A61B 17/068* (2013.01); *A61B 17/0644* (2013.01);
(Continued)

(58) Field of Classification Search
CPC ............ A61B 17/0642; A61B 17/0644; A61B 17/068; A61B 17/0682; A61B 17/10;
(Continued)

(56) References Cited

U.S. PATENT DOCUMENTS

| 752,219 A | 2/1904 | Gold |
|---|---|---|
| 2,010,913 A | 8/1935 | Bruce |

(Continued)

FOREIGN PATENT DOCUMENTS

| CA | 2063484 | 9/1993 |
|---|---|---|
| CN | 2404495 | 11/2000 |

(Continued)

OTHER PUBLICATIONS

U.S. Appl. No. 10/186,402, filed Jan. 22, 2019, Kamata et al.

*Primary Examiner* — Marcela I. Shirsat
(74) *Attorney, Agent, or Firm* — BakerHostetler

(57) ABSTRACT

An implant delivery system includes an implant and an inserter releasably connectable to the implant. When the inserter is connected to the implant, actuating the inserter moves the implant between a free state and an elastically deformed state. The implant has a body with a bone facing surface and bilaterally protruding connecting means. The inserter has hooks that engage under the connecting means. The hooks and the rest of the inserter are proximal to the bone facing surface so that the implant may be fully seated against a bone surface while connected to the inserter.

20 Claims, 12 Drawing Sheets

(51) Int. Cl.
    *A61B 17/10*    (2006.01)
    *A61F 2/08*    (2006.01)
    *A61B 17/00*    (2006.01)
    *A61F 2/46*    (2006.01)

(52) U.S. Cl.
    CPC .......... *A61B 17/0682* (2013.01); *A61B 17/10*
        (2013.01); *A61B 17/0684* (2013.01); *A61B*
        *2017/00867* (2013.01); *A61B 2017/0645*
        (2013.01); *A61B 2017/0648* (2013.01); *A61F*
        *2/0811* (2013.01); *A61F 2/4603* (2013.01);
        *A61F 2220/0025* (2013.01)

(58) Field of Classification Search
    CPC ........ A61B 17/0684; A61B 2017/0645; A61B
        2017/0648; A61B 2017/0688; A61B
        2017/00867; A61F 2/4603; A61F 2/0811
    USPC .......................................................... 606/75
    See application file for complete search history.

(56) References Cited

U.S. PATENT DOCUMENTS

| | | |
|---|---|---|
| 2,133,859 A | 10/1938 | Hawley |
| 2,544,492 A | 3/1951 | Downing |
| 2,811,073 A | 10/1957 | Klopstock |
| 3,741,205 A | 6/1973 | Markolf |
| 4,263,903 A | 4/1981 | Griggs |
| 4,278,091 A | 7/1981 | Borzone |
| 4,415,111 A | 11/1983 | McHarrie |
| 4,438,769 A | 3/1984 | Pratt |
| 4,454,875 A | 6/1984 | Pratt |
| 4,484,570 A | 11/1984 | Sutter |
| 4,655,222 A | 4/1987 | Florez |
| 4,723,540 A | 2/1988 | Gilmer, Jr. |
| 4,805,617 A | 2/1989 | Bedi |
| 4,848,328 A | 7/1989 | Laboureau |
| 4,852,558 A | 8/1989 | Outerbridge |
| 4,874,122 A | 10/1989 | Froelich |
| 5,013,315 A | 5/1991 | Barrows |
| 5,044,540 A | 9/1991 | Dulebohn |
| 5,209,756 A | 5/1993 | Seedhom |
| 5,246,443 A | 9/1993 | Mai |
| 5,258,012 A | 11/1993 | Luscombe |
| 5,352,229 A | 10/1994 | Goble |
| 5,395,372 A | 3/1995 | Holt |
| 5,425,489 A | 6/1995 | Shichman |
| 5,449,359 A | 9/1995 | Groiso |
| 5,454,814 A | 10/1995 | Comte |
| 5,456,400 A | 10/1995 | Shichman et al. |
| 5,490,409 A | 2/1996 | Weber |
| 5,498,749 A | 3/1996 | Heise |
| 5,520,700 A | 5/1996 | Beyar |
| 5,578,034 A | 11/1996 | Estes |
| 5,607,425 A | 3/1997 | Rogozinski |
| 5,628,740 A | 5/1997 | Mullane |
| 5,634,926 A | 6/1997 | Jobe |
| 5,660,188 A | 8/1997 | Groiso |
| 5,662,655 A | 9/1997 | Laboureau |
| 5,716,357 A | 2/1998 | Rogozinski |
| 5,749,564 A | 5/1998 | Malek |
| 5,779,707 A | 7/1998 | Bertholet |
| 5,785,713 A | 7/1998 | Jobe |
| 5,788,698 A | 8/1998 | Savornin |
| 5,807,403 A | 9/1998 | Beyar |
| 5,853,414 A | 12/1998 | Groiso |
| 5,904,682 A | 5/1999 | Rogozinski |
| 5,931,839 A | 8/1999 | Medoff |
| 5,947,968 A | 9/1999 | Rogozinski |
| 5,947,999 A | 9/1999 | Groiso |
| 5,972,000 A | 10/1999 | Beyar |
| 5,993,476 A | 11/1999 | Groiso |
| 6,010,504 A | 1/2000 | Rogozinski |
| 6,017,343 A | 1/2000 | Rogozinski |
| 6,019,759 A | 2/2000 | Rogozinski |
| 6,059,787 A | 5/2000 | Allen |
| 6,089,435 A | 7/2000 | Malek |
| 6,105,936 A | 8/2000 | Malek |
| 6,120,503 A | 9/2000 | Michelson |
| 6,179,840 B1 | 1/2001 | Bowman |
| 6,187,009 B1 | 2/2001 | Herzog |
| 6,281,262 B1 | 8/2001 | Shikinami |
| 6,322,562 B1 | 11/2001 | Wolter |
| 6,334,446 B1 | 1/2002 | Beyar |
| 6,336,927 B2 | 1/2002 | Rogozinski |
| 6,348,054 B1 | 2/2002 | Allen |
| 6,364,884 B1 | 4/2002 | Bowman |
| 6,379,354 B1 | 4/2002 | Rogozinski |
| 6,387,041 B1 | 5/2002 | Harari |
| 6,402,765 B1 | 6/2002 | Monassevitch |
| 6,402,766 B2 | 6/2002 | Bowman |
| 6,406,480 B1 | 6/2002 | Beyar |
| 6,423,073 B2 | 7/2002 | Bowman |
| 6,436,110 B2 | 8/2002 | Bowman |
| 6,447,517 B1 | 9/2002 | Bowman |
| 6,497,707 B1 | 12/2002 | Bowman |
| 6,544,273 B1 | 4/2003 | Harari |
| 6,575,984 B2 | 6/2003 | Beyar |
| 6,575,998 B2 | 6/2003 | Beyar |
| 6,582,435 B2 | 6/2003 | Wellisz |
| 6,592,610 B2 | 7/2003 | Beyar |
| 6,635,058 B2 | 10/2003 | Beyar |
| 6,652,531 B2 | 11/2003 | Wellisz |
| 6,663,642 B2 | 12/2003 | Beyar |
| 6,679,885 B2 | 1/2004 | Wellisz |
| 6,709,437 B2 | 3/2004 | Wellisz |
| 6,730,110 B1 | 5/2004 | Harari |
| 6,746,455 B2 | 6/2004 | Beyar |
| 6,783,531 B2 | 8/2004 | Allen |
| 6,896,684 B2 | 5/2005 | Monassevitch |
| 6,966,911 B2 | 11/2005 | Groiso |
| 6,974,461 B1 | 12/2005 | Wolter |
| 7,044,951 B2 | 5/2006 | Medoff |
| 7,090,676 B2 | 8/2006 | Huebner |
| 7,147,640 B2 | 12/2006 | Huebner |
| 7,153,309 B2 | 12/2006 | Huebner |
| 7,179,260 B2 | 2/2007 | Gerlach |
| 7,189,237 B2 | 3/2007 | Huebner |
| 7,214,232 B2 | 5/2007 | Bowman |
| 7,226,408 B2 | 6/2007 | Harai |
| 7,229,452 B2 | 6/2007 | Kayan |
| 7,235,079 B2 | 6/2007 | Jensen |
| 7,250,054 B2 | 7/2007 | Allen |
| 7,255,701 B2 | 8/2007 | Allen |
| 7,311,712 B2 | 12/2007 | Dalton |
| 7,326,212 B2 | 2/2008 | Huebner |
| 7,438,209 B1 | 10/2008 | Hess |
| 7,473,255 B2 | 1/2009 | McGarity et al. |
| 7,473,257 B2 | 1/2009 | Knöpfle |
| 7,500,979 B2 | 3/2009 | Hueil |
| 7,506,791 B2 | 3/2009 | Omaits |
| 7,537,596 B2 | 5/2009 | Jensen |
| 7,537,603 B2 | 5/2009 | Huebner |
| 7,537,604 B2 | 5/2009 | Huebner |
| 7,556,647 B2 | 7/2009 | Drews |
| 7,562,105 B2 | 7/2009 | Liu |
| 7,578,825 B2 | 8/2009 | Huebner |
| 7,604,151 B2 | 10/2009 | Hess |
| 7,618,441 B2 | 11/2009 | Groiso |
| 7,651,498 B2 | 1/2010 | Shifrin |
| 7,665,647 B2 | 2/2010 | Shelton, IV |
| 7,669,746 B2 | 3/2010 | Shelton, IV |
| 7,669,747 B2 | 3/2010 | Weisenburgh, II |
| 7,673,781 B2 | 3/2010 | Swayze |
| 7,673,782 B2 | 3/2010 | Hess |
| 7,704,251 B2 | 4/2010 | Huebner |
| 7,704,279 B2 | 4/2010 | Moskowitz |
| 7,717,945 B2 | 5/2010 | Jensen |
| 7,735,703 B2 | 6/2010 | Morgan |
| 7,740,634 B2 | 6/2010 | Orbay |
| 7,766,209 B2 | 8/2010 | Baxter, III |
| 7,766,948 B1 | 8/2010 | Leung |
| 7,771,433 B2 | 8/2010 | Orbay |
| 7,794,475 B2 | 9/2010 | Hess |

(56) References Cited

U.S. PATENT DOCUMENTS

| | | |
|---|---|---|
| 7,832,612 B2 | 11/2010 | Baxter, III |
| 7,846,188 B2 | 12/2010 | Moskowitz |
| 7,857,186 B2 | 12/2010 | Baxter, III |
| 7,857,836 B2 | 12/2010 | Huebner |
| 7,867,265 B2 | 1/2011 | Beutter |
| 7,905,381 B2 | 3/2011 | Baxter, III |
| 7,905,910 B2 | 3/2011 | Gerlach |
| 7,909,858 B2 | 3/2011 | Gerlach |
| 7,914,532 B2 | 3/2011 | Shaver |
| 7,918,879 B2 | 4/2011 | Yeung |
| 7,927,332 B2 | 4/2011 | Huebner |
| 7,934,630 B2 | 5/2011 | Shelton, IV |
| 7,935,126 B2 | 5/2011 | Orbay |
| 7,942,903 B2 | 5/2011 | Moskowitz |
| 7,951,180 B2 | 5/2011 | Moskowitz |
| 7,954,686 B2 | 6/2011 | Baxter, III |
| 7,955,388 B2 | 6/2011 | Jensen |
| 7,963,982 B2 | 6/2011 | Kirschman |
| 7,966,799 B2 | 6/2011 | Morgan |
| 7,972,363 B2 | 7/2011 | Moskowitz |
| 8,016,867 B2 | 9/2011 | Bowman |
| 8,043,346 B2 | 10/2011 | Markworth |
| 8,100,953 B2 | 1/2012 | White |
| 8,105,367 B2 | 1/2012 | Austin |
| 8,114,139 B2 | 2/2012 | Sournac |
| 8,137,351 B2 | 3/2012 | Prandi |
| 8,141,762 B2 | 3/2012 | Bedi |
| 8,172,886 B2 | 5/2012 | Castaneda |
| 8,177,819 B2 | 5/2012 | Huebner |
| 8,182,518 B2 | 5/2012 | Butler |
| 8,186,560 B2 | 5/2012 | Hess |
| 8,205,781 B2 | 6/2012 | Baxter, III |
| 8,220,690 B2 | 7/2012 | Hess |
| 8,231,627 B2 | 7/2012 | Huebner |
| 8,231,662 B2 | 7/2012 | Huebner |
| 8,241,326 B2 | 8/2012 | Harari |
| 8,241,338 B2 | 8/2012 | Castaneda |
| 8,252,032 B2 | 8/2012 | White |
| 8,257,370 B2 | 9/2012 | Moskowitz |
| 8,262,711 B2 | 9/2012 | Hess |
| 8,287,543 B2 | 10/2012 | Medoff |
| 8,317,070 B2 | 11/2012 | Hueil |
| 8,337,537 B2 | 12/2012 | Pelo |
| 8,348,129 B2 | 1/2013 | Bedi |
| 8,348,131 B2 | 1/2013 | Omaits |
| 8,353,913 B2 | 1/2013 | Moskowitz |
| 8,360,297 B2 | 1/2013 | Shelton, IV |
| 8,365,976 B2 | 2/2013 | Hess |
| 8,382,807 B2 | 2/2013 | Austin |
| 8,393,517 B2 * | 3/2013 | Milo ............... A61B 17/0644 227/181.1 |
| 8,398,717 B2 | 3/2013 | Kleinman |
| 8,413,872 B2 | 4/2013 | Patel |
| 8,425,574 B2 | 4/2013 | Huebner |
| 8,425,575 B2 | 4/2013 | Huebner |
| 8,425,576 B2 | 4/2013 | Anderson |
| 8,430,292 B2 | 4/2013 | Patel |
| 8,449,561 B2 | 5/2013 | Bowman |
| 8,453,908 B2 | 6/2013 | Bedi |
| 8,464,923 B2 | 6/2013 | Shelton, IV |
| 8,475,504 B2 | 7/2013 | Gillard |
| 8,485,412 B2 | 7/2013 | Shelton, IV |
| 8,486,116 B2 | 7/2013 | Heilman |
| 8,496,693 B2 | 7/2013 | Robinson |
| 8,499,993 B2 | 8/2013 | Shelton, IV |
| 8,518,090 B2 | 8/2013 | Huebner |
| 8,523,919 B2 | 9/2013 | Huebner |
| 8,540,129 B2 | 9/2013 | Baxter, III |
| 8,540,133 B2 | 9/2013 | Bedi |
| 8,545,540 B2 | 10/2013 | Castaneda |
| 8,561,870 B2 | 10/2013 | Baxter, III |
| 8,567,656 B2 | 10/2013 | Shelton, IV |
| 8,574,270 B2 | 11/2013 | Hess |
| 8,584,853 B2 | 11/2013 | Knight |
| 8,585,743 B2 | 11/2013 | Ampuero |
| 8,590,762 B2 | 11/2013 | Hess |
| 8,596,514 B2 | 12/2013 | Miller |
| 8,603,161 B2 | 12/2013 | Drews |
| 8,636,187 B2 | 1/2014 | Hueil |
| 8,652,142 B2 | 2/2014 | Geissler |
| 8,652,180 B2 | 2/2014 | Federspiel |
| 8,657,820 B2 | 2/2014 | Kubiak |
| 8,668,130 B2 | 3/2014 | Hess |
| 8,672,208 B2 | 3/2014 | Hess |
| 8,672,828 B2 | 3/2014 | Harari |
| 8,679,123 B2 | 3/2014 | Kinmon |
| 8,720,766 B2 | 5/2014 | Hess |
| 8,727,197 B2 | 5/2014 | Hess |
| 8,728,128 B2 | 5/2014 | Hawkes |
| 8,728,129 B2 | 5/2014 | Fritzinger |
| 8,734,516 B2 | 5/2014 | Moskowitz |
| 8,740,915 B2 | 6/2014 | Niederberger |
| 8,747,444 B2 | 6/2014 | Moskowitz |
| 8,763,875 B2 | 7/2014 | Morgan |
| 8,777,969 B2 | 7/2014 | Kayan |
| 8,779,927 B2 | 7/2014 | Bell |
| 8,784,450 B2 | 7/2014 | Moskowitz |
| 8,800,838 B2 | 8/2014 | Shelton, IV |
| 8,808,325 B2 | 8/2014 | Hess |
| 8,808,335 B2 | 8/2014 | Biedermann |
| 8,814,915 B2 | 8/2014 | Hess |
| 8,834,537 B2 | 9/2014 | Castaneda |
| 8,858,562 B2 | 10/2014 | Orbay |
| 8,870,882 B2 | 10/2014 | Kleiner |
| 8,882,812 B2 | 11/2014 | Hess |
| 8,888,824 B2 | 11/2014 | Austin |
| 8,888,826 B2 | 11/2014 | Kinmon |
| 8,894,651 B2 | 11/2014 | Aflatoon |
| 8,899,465 B2 | 12/2014 | Shelton, IV |
| 8,906,046 B2 | 12/2014 | Anderson |
| 8,925,788 B2 | 1/2015 | Hess |
| 8,940,028 B2 | 1/2015 | Austin |
| 8,973,804 B2 | 3/2015 | Hess |
| 8,974,504 B2 | 3/2015 | Hess |
| 8,986,305 B2 | 3/2015 | Aflatoon |
| 8,991,676 B2 | 3/2015 | Hess |
| 8,992,581 B2 | 3/2015 | Austin |
| 9,005,206 B2 | 4/2015 | Ampuero |
| 9,005,293 B2 | 4/2015 | Moskowitz |
| 9,017,331 B2 | 4/2015 | Fox |
| 9,017,380 B2 | 4/2015 | Mayer |
| 9,034,037 B2 | 5/2015 | Fiere |
| 9,072,554 B2 | 7/2015 | Reynolds |
| 9,078,757 B2 | 7/2015 | Kleinman |
| 9,095,338 B2 | 8/2015 | Taylor |
| 9,095,388 B2 | 8/2015 | Hess |
| 9,101,349 B2 | 8/2015 | Knight |
| 9,107,661 B2 | 8/2015 | Euteneuer |
| 9,125,650 B2 | 9/2015 | Euteneuer |
| 9,138,233 B2 | 9/2015 | Anderson |
| 9,179,911 B2 | 11/2015 | Morgan |
| 9,180,022 B2 | 11/2015 | Georges |
| 9,204,932 B2 | 12/2015 | Knight |
| 9,220,515 B2 | 12/2015 | Castaneda |
| 9,237,891 B2 | 1/2016 | Shelton, IV |
| 9,247,978 B2 | 2/2016 | Euteneuer |
| 9,265,649 B2 | 2/2016 | Pflueger |
| D752,219 S | 3/2016 | Peterson |
| 9,271,726 B2 | 3/2016 | Euteneuer |
| 9,283,006 B2 | 3/2016 | Fonte |
| 9,289,206 B2 | 3/2016 | Hess |
| 9,289,210 B2 | 3/2016 | Baxter, III |
| 9,301,854 B2 | 4/2016 | Moskowitz |
| 9,307,988 B2 | 4/2016 | Shelton, IV |
| 9,308,033 B2 | 4/2016 | Huebner |
| 9,326,768 B2 | 5/2016 | Shelton, IV |
| 9,326,771 B2 | 5/2016 | Baxter, III |
| 9,339,268 B2 | 5/2016 | Fox |
| 9,370,355 B2 | 6/2016 | Anderson |
| 9,370,356 B2 | 6/2016 | Euteneuer |
| 9,370,376 B2 | 6/2016 | Castaneda |
| 9,387,116 B2 | 7/2016 | Pflueger |
| 9,402,623 B2 | 8/2016 | Kayan |
| 9,402,624 B1 | 8/2016 | Scott |

(56) References Cited

U.S. PATENT DOCUMENTS

| | | |
|---|---|---|
| 9,408,603 B2 | 8/2016 | Patel |
| 9,408,604 B2 | 8/2016 | Shelton, IV |
| 9,408,647 B2 | 8/2016 | Cheney |
| 9,414,841 B2 | 8/2016 | Euteneuer |
| 9,414,871 B2 | 8/2016 | Huebner |
| 9,421,013 B2 | 8/2016 | Patel |
| 9,445,808 B2 | 9/2016 | Woodard, Jr. |
| 9,451,957 B2 | 9/2016 | Fox |
| 9,463,015 B2 | 10/2016 | Hausen |
| 9,486,212 B2 | 11/2016 | Miller |
| 9,532,821 B2 | 1/2017 | Moskowitz |
| 9,539,023 B2 | 1/2017 | Marotte |
| 9,549,735 B2 | 1/2017 | Shelton, IV |
| 9,561,032 B2 | 2/2017 | Shelton, IV |
| 9,566,063 B2 | 2/2017 | Euteneuer |
| 9,603,641 B2 | 3/2017 | Hulliger |
| 9,615,856 B2 | 4/2017 | Arnett |
| 9,763,715 B2 | 9/2017 | Mather |
| 9,839,458 B2 | 12/2017 | Bouduban |
| 9,861,404 B2 | 1/2018 | Reiley |
| 9,918,762 B2 | 3/2018 | Federspiel et al. |
| 9,924,984 B2 | 3/2018 | Hartdegen |
| 9,955,964 B2 | 5/2018 | Mayer |
| 10,166,022 B2 | 1/2019 | Early |
| 10,292,743 B2 | 5/2019 | Taylor |
| 10,299,842 B2 | 5/2019 | Hollis |
| 10,357,986 B2 | 7/2019 | Zhou |
| 10,433,885 B2 | 10/2019 | Hartdegen |
| 10,448,979 B2 | 10/2019 | Fox |
| D870,284 S | 12/2019 | Hollis et al. |
| D892,331 S | 8/2020 | Hollis et al. |
| 2001/0028148 A1 | 10/2001 | White |
| 2002/0095155 A1 | 7/2002 | Michelson |
| 2002/0095181 A1 | 7/2002 | Beyar |
| 2002/0111641 A1 | 8/2002 | Peterson |
| 2003/0083663 A1 | 5/2003 | Goldhahn |
| 2003/0158553 A1 | 8/2003 | Michelson |
| 2003/0225409 A1 | 12/2003 | Freid |
| 2004/0073222 A1 | 4/2004 | Koseki |
| 2004/0127896 A1 | 7/2004 | Lombardo |
| 2004/0172040 A1 | 9/2004 | Heggeness |
| 2004/0220570 A1 | 11/2004 | Frigg |
| 2005/0021032 A1 | 1/2005 | Koo |
| 2005/0021035 A1 | 1/2005 | Groiso |
| 2005/0043757 A1 | 2/2005 | Arad |
| 2005/0049600 A1 | 3/2005 | Groiso |
| 2005/0085818 A1 | 4/2005 | Huebner |
| 2005/0096660 A1 | 5/2005 | Allen |
| 2005/0101961 A1 | 5/2005 | Huebner |
| 2005/0107796 A1 | 5/2005 | Gerlach |
| 2005/0119667 A1 | 6/2005 | Leport |
| 2005/0165400 A1 | 7/2005 | Fernandez |
| 2005/0171544 A1 | 8/2005 | Falkner |
| 2005/0234458 A1 | 10/2005 | Huebner |
| 2005/0240187 A1 | 10/2005 | Huebner |
| 2006/0058796 A1 | 3/2006 | Hartdegen |
| 2006/0058802 A1 | 3/2006 | Kofoed |
| 2006/0106391 A1 | 5/2006 | Huebner |
| 2006/0122604 A1 | 6/2006 | Gorhan |
| 2006/0122605 A1 | 6/2006 | Suh |
| 2006/0129151 A1 | 6/2006 | Allen |
| 2006/0200147 A1 | 9/2006 | Ensign |
| 2006/0241612 A1 | 10/2006 | Medoff |
| 2006/0241618 A1 | 10/2006 | Gasser |
| 2006/0264936 A1 | 11/2006 | Partin |
| 2007/0055249 A1 | 3/2007 | Jensen |
| 2007/0173840 A1 | 7/2007 | Huebner |
| 2007/0191850 A1 | 8/2007 | Kim et al. |
| 2007/0208358 A1 | 9/2007 | Kayan |
| 2007/0233116 A1 | 10/2007 | Olerud |
| 2008/0147125 A1 | 6/2008 | Colleran |
| 2008/0195099 A1 | 8/2008 | Minas |
| 2008/0200955 A1 | 8/2008 | Tepic |
| 2008/0255620 A1 | 10/2008 | Strauss |
| 2008/0275510 A1 | 11/2008 | Schonhardt |
| 2008/0288000 A1 | 11/2008 | Cawley |
| 2008/0319443 A1 | 12/2008 | Focht |
| 2009/0054930 A1 | 2/2009 | Aflatoon |
| 2009/0138082 A1 | 5/2009 | Reah |
| 2009/0177203 A1 | 7/2009 | Reiley |
| 2009/0182383 A1 | 7/2009 | Prybyla |
| 2009/0187247 A1 | 7/2009 | Metcalf, Jr. |
| 2009/0254090 A1 | 10/2009 | Lizee |
| 2009/0254126 A1 | 10/2009 | Orbay |
| 2009/0281543 A1 | 11/2009 | Orbay |
| 2010/0036430 A1 | 2/2010 | Hartdegen |
| 2010/0076448 A1 | 3/2010 | Abdou |
| 2010/0082065 A1 | 4/2010 | Butler |
| 2010/0100138 A1 | 4/2010 | Reynolds |
| 2010/0106196 A1 | 4/2010 | Erickson |
| 2010/0133316 A1 | 6/2010 | Lizee |
| 2010/0211116 A1 | 8/2010 | Suh |
| 2010/0256765 A1 | 10/2010 | Butler |
| 2010/0292715 A1 | 11/2010 | Nering |
| 2010/0312280 A1 | 12/2010 | Overes |
| 2011/0022049 A1 | 1/2011 | Huebner |
| 2011/0022099 A1 | 1/2011 | Ashman |
| 2011/0029016 A1 | 2/2011 | Yeung |
| 2011/0029023 A1 | 2/2011 | Tornier |
| 2011/0029025 A1 | 2/2011 | Medoff |
| 2011/0054542 A1 | 3/2011 | Kevin |
| 2011/0092981 A1 | 4/2011 | Ng |
| 2011/0098754 A1 | 4/2011 | Hulliger |
| 2011/0118796 A1 | 5/2011 | Reiley |
| 2011/0118840 A1 | 5/2011 | Huntsman |
| 2011/0202092 A1 | 8/2011 | Frigg |
| 2011/0270326 A1 | 11/2011 | Black |
| 2011/0282393 A1 | 11/2011 | Gerlach |
| 2011/0295324 A1 | 12/2011 | Donley |
| 2011/0313421 A1 | 12/2011 | Sidebotham |
| 2011/0319942 A1 | 12/2011 | Bottlang |
| 2012/0022600 A1 | 1/2012 | Overes |
| 2012/0024937 A1 | 2/2012 | Allen |
| 2012/0053638 A1 | 3/2012 | Rusch |
| 2012/0065690 A1 | 3/2012 | Perrow |
| 2012/0078371 A1 | 3/2012 | Gamache |
| 2012/0095513 A1 | 4/2012 | Humphreys |
| 2012/0136396 A1 | 5/2012 | Baker |
| 2012/0143193 A1 | 6/2012 | Hulliger |
| 2012/0150240 A1 | 6/2012 | Medoff |
| 2012/0179207 A1 | 7/2012 | Mekhail |
| 2012/0191141 A1 | 7/2012 | Costabile |
| 2012/0323284 A1 | 12/2012 | Baker |
| 2013/0006247 A1 | 1/2013 | Weiner |
| 2013/0023938 A1 | 1/2013 | Huebner |
| 2013/0023940 A1 | 1/2013 | Hansell |
| 2013/0026206 A1 | 1/2013 | Fox |
| 2013/0030437 A1 | 1/2013 | Fox |
| 2013/0046346 A1 | 2/2013 | Thorwarth |
| 2013/0109910 A1 | 5/2013 | Alexander |
| 2013/0138154 A1 | 5/2013 | Reiley |
| 2013/0150900 A1 | 6/2013 | Haddad |
| 2013/0218285 A1 | 8/2013 | Kleinman |
| 2013/0226252 A1 | 8/2013 | Mayer |
| 2013/0238035 A1 | 9/2013 | Medoff |
| 2013/0267956 A1 | 10/2013 | Terrill |
| 2013/0303071 A1 | 11/2013 | Seki |
| 2013/0325074 A1 | 12/2013 | Ziolo |
| 2013/0345752 A1 | 12/2013 | Hendren |
| 2014/0014553 A1 | 1/2014 | Knight |
| 2014/0018809 A1 | 1/2014 | Allen |
| 2014/0018862 A1 | 1/2014 | Koay |
| 2014/0020333 A1 | 1/2014 | Knight |
| 2014/0024002 A1 | 1/2014 | Knight |
| 2014/0034702 A1 | 2/2014 | Miller |
| 2014/0058461 A1 | 2/2014 | Black |
| 2014/0100652 A1 | 4/2014 | Drews |
| 2014/0142628 A1 | 5/2014 | Traynelis |
| 2014/0163621 A1 | 6/2014 | Huebner |
| 2014/0163682 A1 | 6/2014 | Iott |
| 2014/0163683 A1 | 6/2014 | Seifert |
| 2014/0172026 A1 | 6/2014 | Biedermann |
| 2014/0200670 A1 | 7/2014 | Chin |
| 2014/0207195 A1 | 7/2014 | Appenzeller |

(56) References Cited

U.S. PATENT DOCUMENTS

| | | |
|---|---|---|
| 2014/0222086 A1 | 8/2014 | Kuster |
| 2014/0276830 A1 | 9/2014 | Cheney |
| 2014/0296925 A1 | 10/2014 | Lawson |
| 2014/0309639 A1 | 10/2014 | Averous et al. |
| 2014/0316470 A1 | 10/2014 | Hartdegen |
| 2014/0358187 A1 | 12/2014 | Taber |
| 2015/0012003 A1 | 1/2015 | Ryan |
| 2015/0045804 A1 | 2/2015 | Orbay |
| 2015/0066095 A1 | 3/2015 | Austin |
| 2015/0080914 A1 | 3/2015 | Roundy |
| 2015/0080969 A1 | 3/2015 | Holly |
| 2015/0133940 A1 | 5/2015 | Palmer |
| 2015/0142063 A1 | 5/2015 | Austin |
| 2015/0148850 A1 | 5/2015 | Orbay |
| 2015/0173749 A1 | 6/2015 | Shelton, IV |
| 2015/0173750 A1 | 6/2015 | Shelton, IV |
| 2015/0173751 A1 | 6/2015 | Shelton, IV |
| 2015/0173756 A1 | 6/2015 | Baxter, III |
| 2015/0196333 A1 | 7/2015 | Austin |
| 2015/0216570 A1 | 8/2015 | Hess |
| 2015/0216573 A1 | 8/2015 | Chin |
| 2015/0238191 A1 | 8/2015 | Schellin |
| 2015/0282819 A1 | 10/2015 | Austin |
| 2015/0313592 A1 | 11/2015 | Coillard-Lavirotte |
| 2015/0320462 A1 | 11/2015 | Biedermann |
| 2015/0351762 A1 | 12/2015 | Vendely |
| 2015/0351763 A1 | 12/2015 | Shelton, IV |
| 2015/0351764 A1 | 12/2015 | Shelton, IV |
| 2016/0015384 A1 | 1/2016 | Roedl |
| 2016/0066907 A1 | 3/2016 | Cheney |
| 2016/0074037 A1 | 3/2016 | Cheney |
| 2016/0089191 A1 | 3/2016 | Pak |
| 2016/0100835 A1 | 4/2016 | Linder |
| 2016/0157906 A1 | 6/2016 | Hollis |
| 2016/0192930 A1 | 7/2016 | Finley et al. |
| 2016/0199060 A1* | 7/2016 | Morgan ................. A61B 17/10 227/175.1 |
| 2016/0235460 A1 | 8/2016 | Wahl |
| 2016/0242771 A1 | 8/2016 | Weinstein |
| 2016/0242927 A1 | 8/2016 | Seifert |
| 2016/0331372 A1 | 11/2016 | Nelson |
| 2016/0338697 A1* | 11/2016 | Biedermann ...... A61B 17/0642 |
| 2016/0354117 A1 | 12/2016 | Nakaji |
| 2017/0000482 A1 | 1/2017 | Averous et al. |
| 2017/0000533 A1 | 1/2017 | Fallin |
| 2017/0065276 A1 | 3/2017 | Weiner et al. |
| 2017/0065312 A1 | 3/2017 | Lauf |
| 2017/0112553 A1 | 4/2017 | Hansell |
| 2017/0119443 A1 | 5/2017 | Cawley |
| 2017/0156776 A1 | 6/2017 | Weiman |
| 2017/0164990 A1 | 6/2017 | Weiner |
| 2017/0181779 A1 | 6/2017 | Leither |
| 2017/0196604 A1* | 7/2017 | Hartdegen ......... A61B 17/8085 |
| 2017/0196606 A1 | 7/2017 | Cianfrani |
| 2017/0202552 A1 | 7/2017 | Coleman |
| 2017/0202585 A1 | 7/2017 | Leak |
| 2017/0209193 A1 | 7/2017 | Hartdegen |
| 2017/0231625 A1* | 8/2017 | Handie .................. A61B 17/10 227/175.1 |
| 2017/0238974 A1 | 8/2017 | Konieczynski |
| 2017/0245901 A1 | 8/2017 | Grigorian |
| 2017/0281157 A1* | 10/2017 | Hartdegen ........... A61B 17/846 |
| 2017/0354509 A1 | 12/2017 | Finley |
| 2018/0000592 A1 | 1/2018 | Mayer |
| 2018/0296257 A1 | 10/2018 | Penzimer |
| 2018/0317906 A1 | 11/2018 | Hollis |
| 2018/0353172 A1 | 12/2018 | Hartdegen |
| 2019/0000451 A1 | 1/2019 | Majors et al. |
| 2019/0046182 A1 | 2/2019 | Krumme |
| 2019/0046183 A1 | 2/2019 | Hartdegen |
| 2019/0150921 A1 | 5/2019 | Fonte et al. |
| 2020/0000464 A1 | 1/2020 | Gaston et al. |
| 2020/0000465 A1 | 1/2020 | Maclure et al. |

FOREIGN PATENT DOCUMENTS

| | | |
|---|---|---|
| DE | 3119550 | 12/1982 |
| DE | 29721858 | 3/1998 |
| DE | 19821680 | 8/1999 |
| DE | 20001879 | 5/2000 |
| DE | 102004015223 | 10/2005 |
| EP | 0092383 | 11/1987 |
| EP | 0253629 A1 | 1/1988 |
| EP | 0768062 | 4/1997 |
| EP | 0826340 | 3/1998 |
| EP | 0857462 | 8/1998 |
| EP | 0682920 | 5/2000 |
| EP | 0867149 B1 | 9/2000 |
| EP | 1870042 | 7/2009 |
| EP | 2231044 | 3/2012 |
| EP | 3082632 A1 | 10/2016 |
| EP | 3166505 A1 | 5/2017 |
| EP | 3166522 A1 | 5/2017 |
| EP | 3179939 A1 | 6/2017 |
| FR | 2628312 | 9/1989 |
| FR | 2694696 | 11/1994 |
| FR | 2725126 | 4/1997 |
| FR | 2758252 B1 | 4/1999 |
| FR | 2874316 | 10/2006 |
| FR | 2927527 | 8/2009 |
| FR | 2874166 | 3/2012 |
| FR | 2935256 | 3/2012 |
| FR | 2980966 | 11/2013 |
| GB | 2118474 A | 11/1983 |
| GB | 2471648 | 1/2012 |
| WO | WO1992017122 | 10/1992 |
| WO | WO2001056489 | 8/2001 |
| WO | 03/68081 A1 | 8/2003 |
| WO | 03/71962 A2 | 9/2003 |
| WO | 2008/007196 A2 | 1/2008 |
| WO | WO2008129061 | 10/2008 |
| WO | 2009/091770 A1 | 7/2009 |
| WO | WO2010004602 | 1/2010 |
| WO | 2011/014547 A1 | 2/2011 |
| WO | 2011/110916 A1 | 9/2011 |
| WO | 2012/071129 A2 | 5/2012 |
| WO | 2013/010282 A1 | 1/2013 |
| WO | 2013/055824 A1 | 4/2013 |
| WO | 2013/130978 A2 | 9/2013 |
| WO | WO2013186205 | 12/2013 |
| WO | WO2015004391 | 1/2015 |
| WO | 2015/095126 A1 | 6/2015 |
| WO | WO2015107311 | 7/2015 |
| WO | 2016/007624 A1 | 1/2016 |
| WO | 2016/007626 A1 | 1/2016 |
| WO | 2016/025162 A1 | 2/2016 |
| WO | WO2016110760 | 7/2016 |
| WO | 2017/011589 A1 | 1/2017 |
| WO | 2017/139315 A1 | 8/2017 |
| WO | 2017/139328 A1 | 8/2017 |
| WO | 2018/145064 A1 | 8/2018 |
| WO | 2018/148284 A1 | 8/2018 |

* cited by examiner

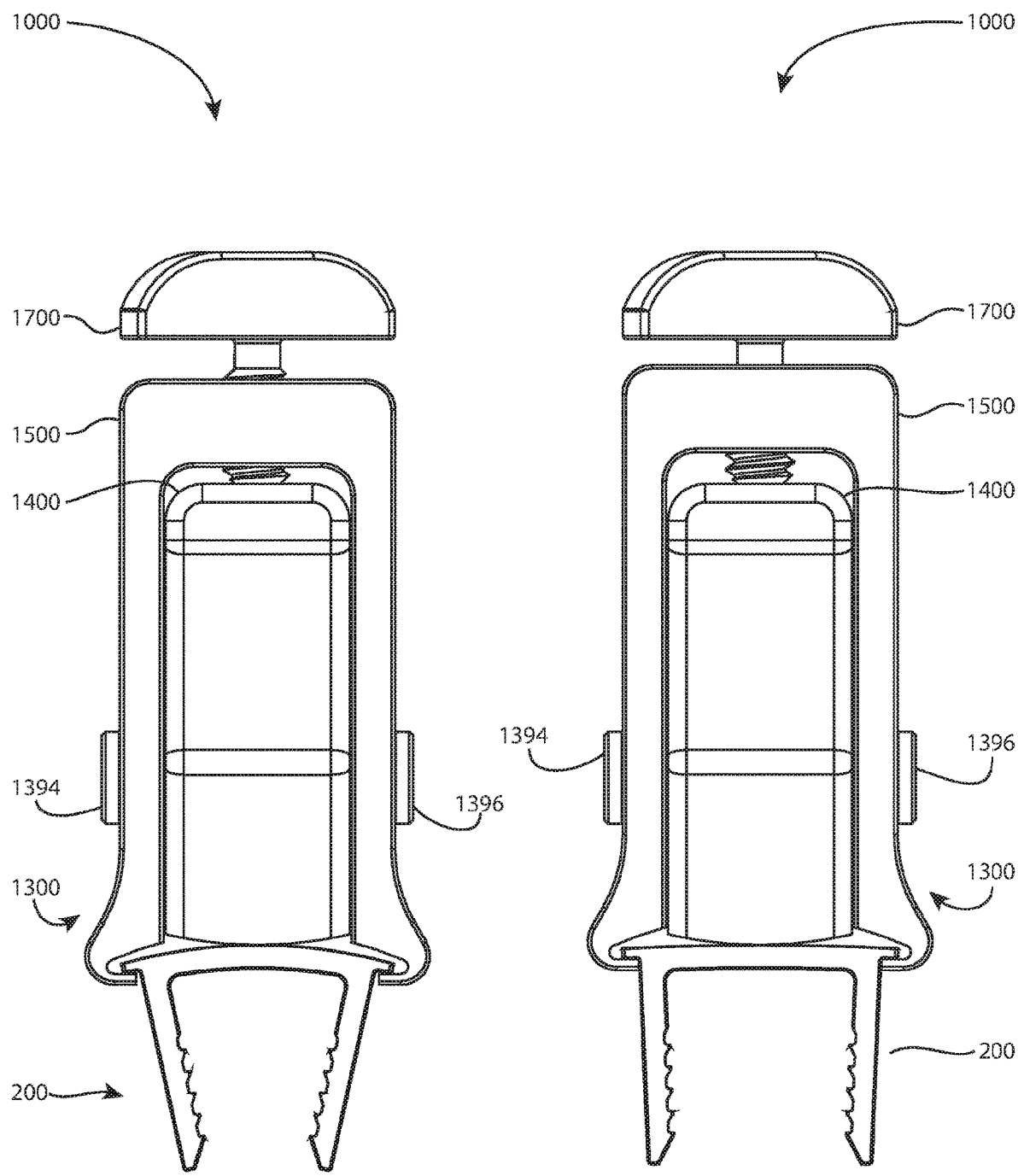

IMPLANT INSERTER

TECHNICAL FIELD

The present disclosure relates to an implant and a corresponding inserter. More specifically, the present disclosure is made in the context of a bone staple and a corresponding inserter. However, the disclosed technology is broadly applicable outside this context, as will be apparent to one of skill in the art.

The staple has a free state, or relaxed state, which is its shape when no external forces are acting upon the staple, other than gravity perhaps. In the free state, the staple is not elastically or plastically deflected or deformed. The staple may experience loads that are below a threshold for elastic or plastic deflection or deformation. In the free state, the staple legs converge at their distal tips. The staple may be made from high elasticity materials such as nitinol and/or polyetheretherketone (PEEK) so that the staple may be elastically deformed by an external force, and then resume the free state when the external force is removed.

The inserter securely and releasably couples to the staple. When actuated, the inserter urges the staple out of the free state into a continuum of elastically deformed states in which the staple legs a) progressively approach a parallel condition, b) achieve a parallel condition, or c) progressively diverge at their distal tips. When the inserter is uncoupled from the bone staple, the bone staple resumes the free state, or attempts to do so. When the bone staple is implanted in bone, then the staple may only be able to partially relax toward the free state due to the resistance of the bone.

SUMMARY

In an aspect of the technology, an implant delivery system includes: an implant including a body, a first bone engagement member, a second bone engagement member, a first connecting means, and a second connecting means, wherein the body extends between a first end and an opposite second end to establish a longitudinal direction of the body, wherein the first bone engagement member extends from the first end transverse to the body, wherein the second bone engagement member extends from the second end transverse to the body beside the first bone engagement member, wherein the first connecting means extends outwardly from the first end along the longitudinal direction, wherein the second connecting means extends outwardly from the second end along the longitudinal direction, wherein the implant includes an implant free state in which the first and second bone engagement members converge as they extend from the body, and an elastically deformed state in which the first and second bone engagement members are spread apart relative to the implant free state; and an inserter removably connectable to the implant, the inserter including a first hook, a second hook, and a ram pin, wherein the first and second hooks face each other and are movable proximally and distally relative to the ram pin; wherein when the inserter is connected to the implant, the first hook receives the first connecting means and the second hook receives the second connecting means, wherein moving the first and second hooks proximally relative to the ram pin causes the body to elastically deform against the resistance of the ram pin to move the implant into the elastically deformed state.

In another aspect of the technology, an implant delivery system includes: an implant including a body, a first connection feature, and a second connection feature, wherein the implant body includes a proximal surface and an opposite distal surface, wherein the implant body extends between a first end and an opposite second end to establish a longitudinal direction of the implant body, wherein the first connection feature includes a distal surface that is offset from the implant body distal surface toward the implant body proximal surface, wherein the first connection feature is at the first end, wherein the second connection feature includes a distal surface that is offset from the implant body distal surface toward the implant body proximal surface, wherein the second connection feature is at the second end, wherein the implant is movable between a free state and an elastically deformed state; and an inserter that is removably connectable to the implant, wherein the inserter includes a third connection feature, a fourth connection feature, and a static support, wherein the third and fourth connection features are movable proximally and distally relative to the static support; wherein when the inserter is connected to the implant, the first connection feature engages the third connection feature, the second connection feature engages the fourth connection feature, the implant body proximal surface faces the static support, and the entire inserter is proximal to the implant body distal surface; wherein moving the third and fourth connection features proximally and distally relative to the static support moves the implant between the free state and the elastically deformed state.

Embodiments of this aspect may include one or more of the following attributes. The first connection feature extends outwardly from the first end along the longitudinal direction, wherein the second connection feature extends outwardly from the second end along the longitudinal direction. The implant includes a first fixation member and a second fixation member, wherein the first fixation member is at the first end, wherein the second fixation member is at the second end. The first and second fixation members extend from the implant body distal surface. The first and second connection features are lateral to the first and second fixation members. In the free state, the first and second fixation members converge as they extend from the implant body, wherein in the elastically deformed state, the first and second fixation members are spread apart relative to the free state. When the inserter is connected to the implant, the first connection feature distal surface engages a proximal surface of the third connection feature and the second connection feature distal surface engages a proximal surface of the fourth connection feature. Moving the third and fourth connection features proximally relative to the static support causes the implant body to elastically deform against the static support to move the implant into the elastically deformed state. The inserter includes a distal groove, wherein when the inserter is connected to the implant, a proximal portion of the implant body is received in the distal groove. The static support is located within the distal groove. The static support remains in contact with the implant body proximal surface at all times while the inserter is connected to the implant.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 17 is a front view of the system of FIG. 11 with the implant in a free state and a jaw member of the inserter in a distal position; and FIG. 18 is a front view of the system of FIG. 11 with the implant in an elastically deformed state and the jaw member of the inserter in a proximal position.

DETAILED DESCRIPTION

Figure 1:
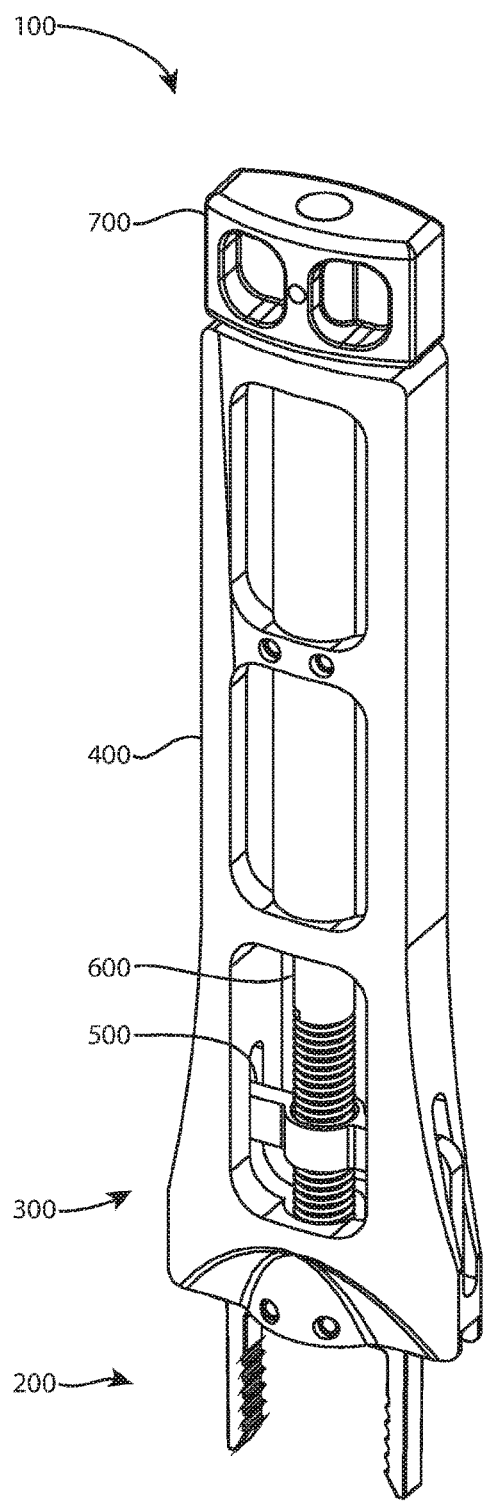
FIG. 1 is a perspective view of a system with an implant coupled to an inserter.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

Figure 2:
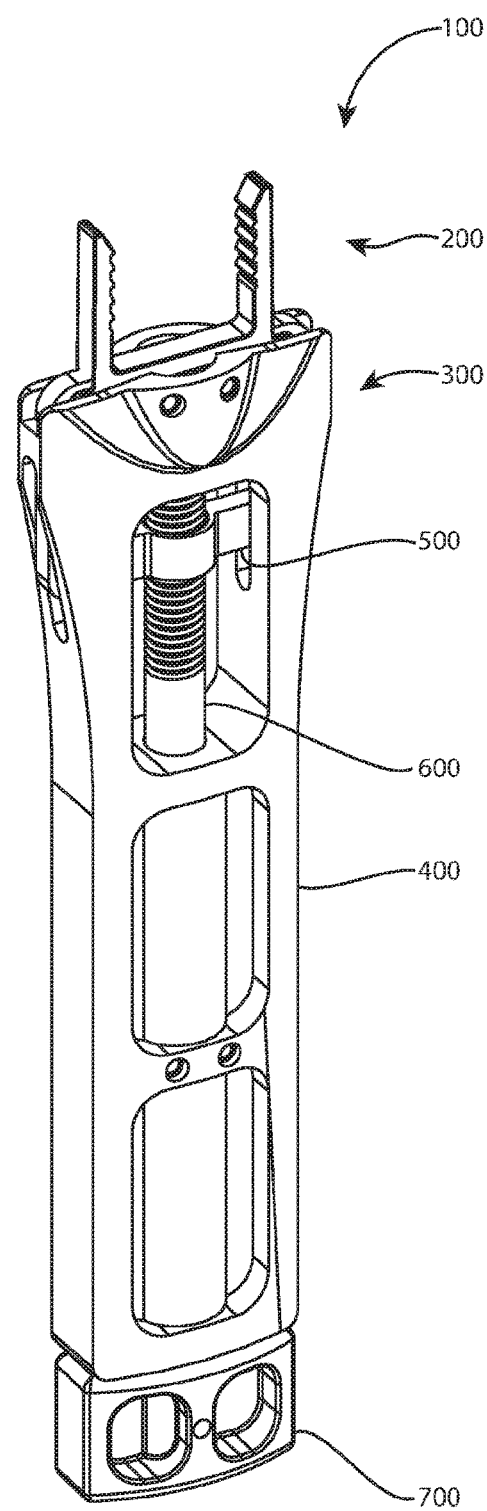
FIG. 2 is another perspective view of the system of FIG. 1 from a different direction.

Referring to FIGS. 1 and 2, an implant delivery system 100 includes an implant 200 and an inserter 300. The implant 200 is shown coupled to the inserter 300, the implant in an elastically deformed state. The illustrated implant 200 is a compression bone staple.

The implant 200 may be identical to the implant embodiment 2200 described in International Patent Application Serial No. PCT/US2015/039551.

Figure 3:
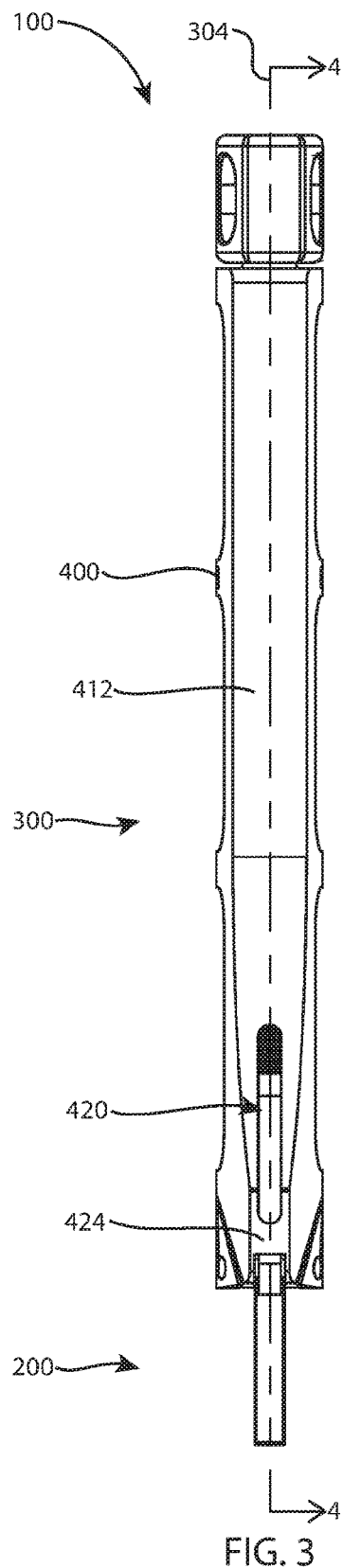
FIG. 3 is a side view of the system of FIG. 1.
Figure 4:
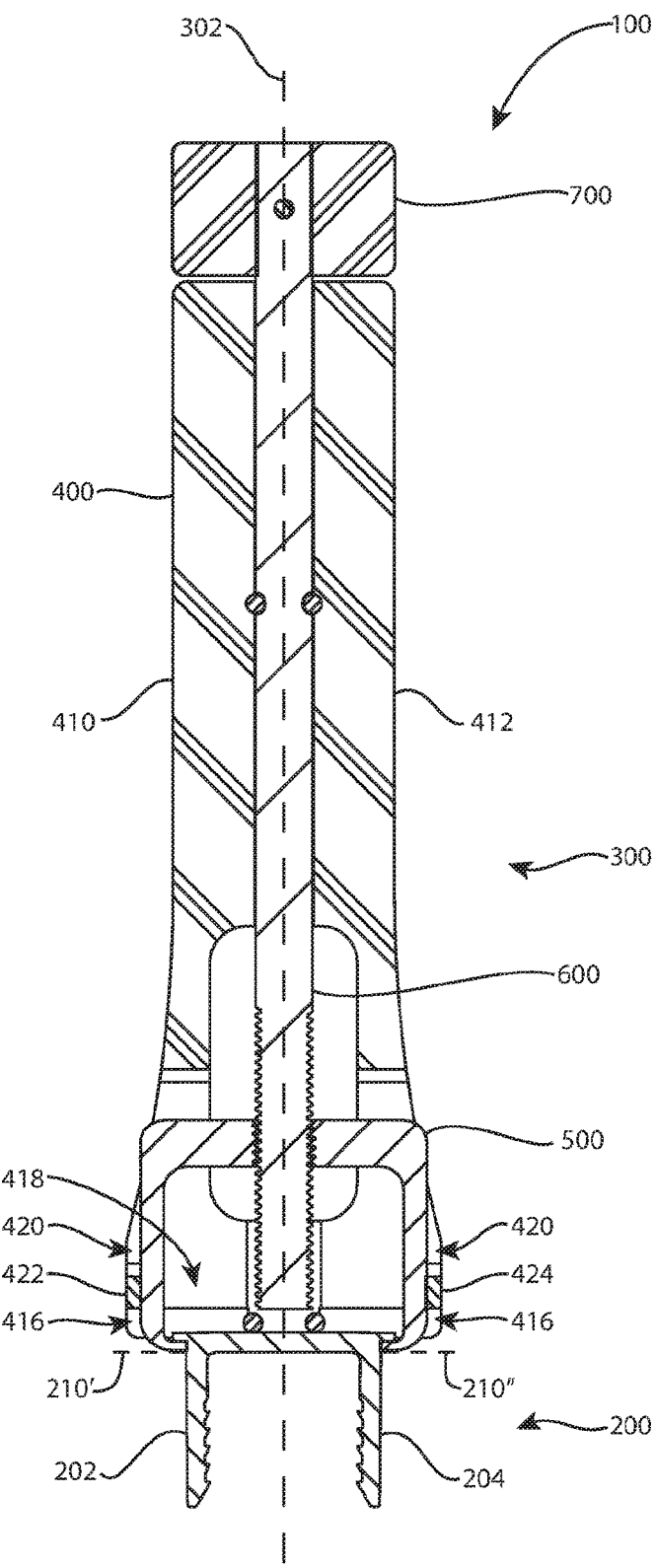
FIG. 4 is a cross sectional view of the system of FIG. 1, taken along section line 4-4 of FIG. 3.
Figure 9:
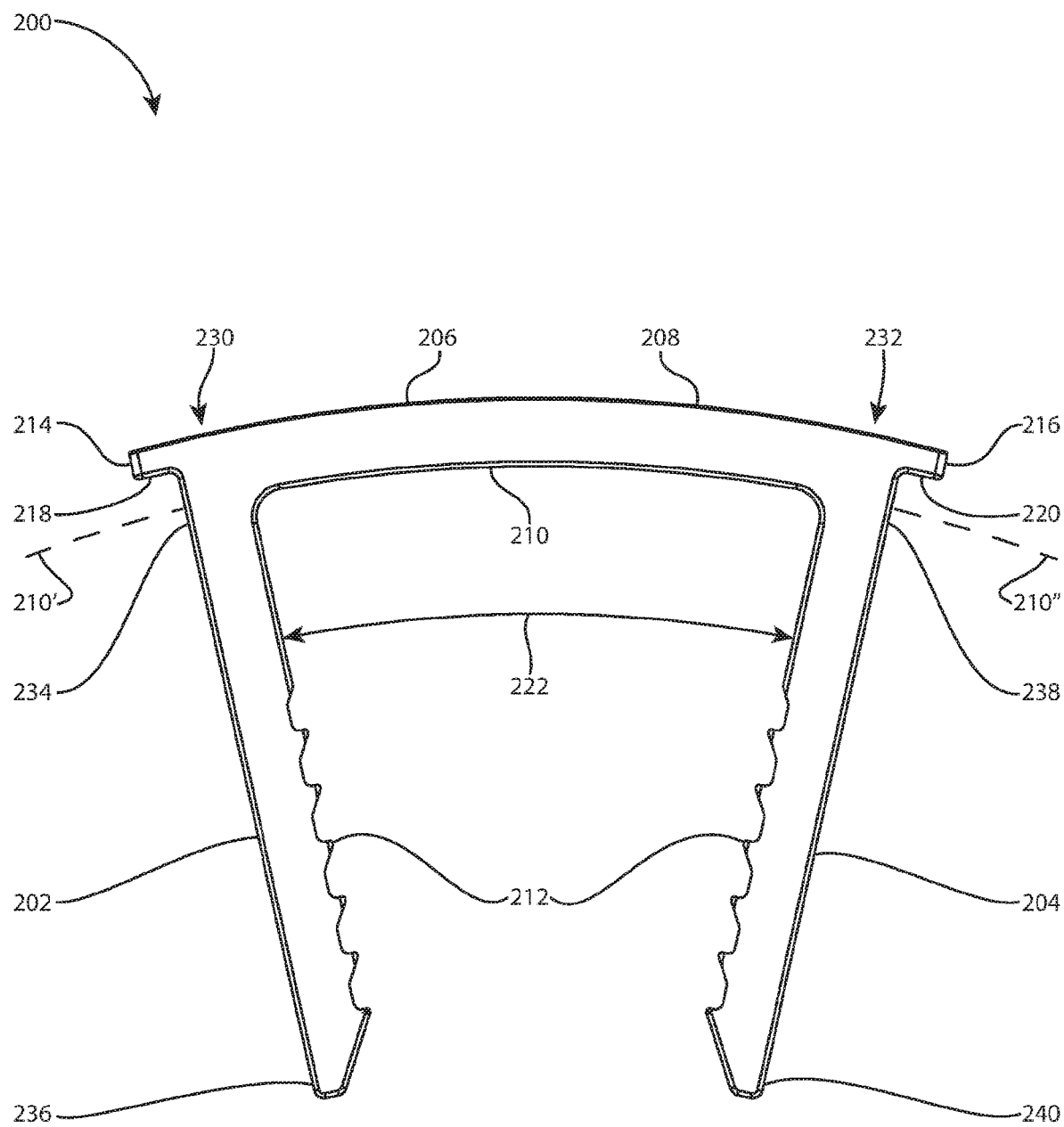
FIG. 9 is a front view of the implant of FIG. 1.

Referring to FIGS. 1-6 and 9, the implant 200 may include bone engaging members 202 and 204 which may be integral to an implant bridge 206, also referred to as an implant body. Alternatively, the bone engaging members 202, 204 may be separate parts that are connected to the implant body. The bone engaging members 202 and 204 may be referred to as legs or fixation members. The bone engaging member 202 extends from a left end 230 of the implant bridge 206 and the bone engaging member 204 extends from an opposite right end 232 of the implant bridge 206. Bone engaging member 202 has a proximal end 234 attached to the left end 230 of the implant bridge 206 and an opposite distal end 236 which is a free end. Bone engaging member 204 has a proximal end 238 attached to the right end 232 of the implant bridge 206 and an opposite distal end 240 which is a free end. Implant bridge 206 has an upper surface 208 and a lower surface 210. The upper surface 208 may be referred to as a proximal surface. The lower surface 210 may be referred to as a bone facing surface or a distal surface. Bone engaging member 202 extends from the lower surface 210 beside bone engaging member 204. The bone engaging members 202 and 204 may have features 212 that may improve bone purchase or improve pull out strength of the implant 200 from bone or soft tissue. The features 212 may be referred to as teeth or serrations. The features 212 are shown on facing sides of the bone engaging members 202, 204 but may be on any or all sides of the bone engaging members. The implant 200 may have projections or other connecting means 214 and 216 for connection with a means of insertion, such as inserter 300. The connecting means 214, 216 may be referred to as tabs, ears, protrusions, retainers, wings, retaining members, or connection features. The connecting means 214 and 216 are shown extending sideways outwardly from the ends 230, 232 of the bridge 206, respectively, along a longitudinal direction established between the left and right ends 230, 232 of the bridge. The connecting means 214 and 216 are shown lateral to the bone engaging members 202 and 204. However, in other examples, the connecting means may extend outwardly from the ends of the bridge along a front to back direction. These examples may include four connecting means: left front, left back, right front, and right back. The connecting means 214 and 216 may have lower surfaces 218 and 220 respectively that may releasably engage with a means of insertion that may allow the inserter 300 or other means of insertion to be side loading, top loading or pivotably loaded. For example, the inserter 300 may be described as side loading or pivotably loading. The lower surfaces 218, 220 may be referred to as bone facing surfaces or distal surfaces. Referring to FIGS. 4 and 9, the lower surfaces 218, 220 are proximally spaced apart, or proximally offset, from the lower surface 210 toward the upper surface 208. The dashed extension lines 210' and 210" in FIGS. 4 and 9 show the level of the lower surface 210 versus the lower surfaces 218, 220.

The means of insertion may maintain an implant in a first configuration thereby allowing a second implant configuration once the implant is disassembled from the implant. The first configuration may be an elastically deformed state, for example an insertion state. The second configuration may be a free state or an implanted state. The means of insertion may utilize features similar to connecting means 214 and 216 in combination with other surfaces such as top surface 208. This combination of means of insertion may be used to maintain one or more features or arms or projections in a particular configuration. This combination of means of insertion may create a bending modality, such as a three point or four point bend, to maintain a specific implant configuration or combination of configurations. A combination of surfaces and means of insertion, such as connecting means 214, may be used on the entire implant or portions of an implant to create or maintain a particular configuration of an implant. For example, a tab such as 214 and top surface, such as 208 may be used to maintain one side of an implant or one arm of an implant in a particular configuration. When disassembled, that arm may have a configuration that is different from or the same as the configuration of the rest of the implant.

Referring to FIG. 9, the implant 200 is shown uncoupled from the inserter 300. The implant 200 is in a free state, or relaxed state, which is the shape of the implant 200 when no external forces are acting upon the implant 200, other than gravity perhaps; the implant 200 experiences no elastic or plastic deflection or deformation. However, in the free state, the implant 200 may experience loads that are below a threshold for elastic or plastic deflection or deformation. In the free state, the bone engaging members 202 and 204 converge as they extend away from the bridge 206 so that the distal ends 236, 240 are closer together than the proximal ends 234, 238. An angle 222 is formed between the converging bone engaging members 202 and 204 in the free state. The angle 222 opens toward the bridge 206. The angle 222 may be referred to as a free state angle.

The implant 200 may be moved between the free state and an elastically deformed state by elastically deforming some or all of the implant 200. For example, elastically deforming or pressing on the bridge 206 so that it bows down between the bone engaging members 202, 204 causes the distal ends 236, 240 to spread apart. Alternatively, the bone engaging members 202, 204 may be elastically deformed so that the distal ends 236, 240 spread apart or come closer together. The bone engaging members 202, 204 may spread apart in the elastically deformed state so as to become parallel as seen best in FIG. 4. The elastically deformed state may be suitable for implantation of the implant 200, and may thus be referred to as an insertion state or an implantation state.

Referring to FIGS. 1-6, the inserter 300 may include a body 400, a jaw member 500, a drive shaft 600, a knob 700, a left ram pin 394, a right ram pin 396, a left drive shaft pin 390, a right drive shaft pin 392, and a knob pin 398.

Figure 7:
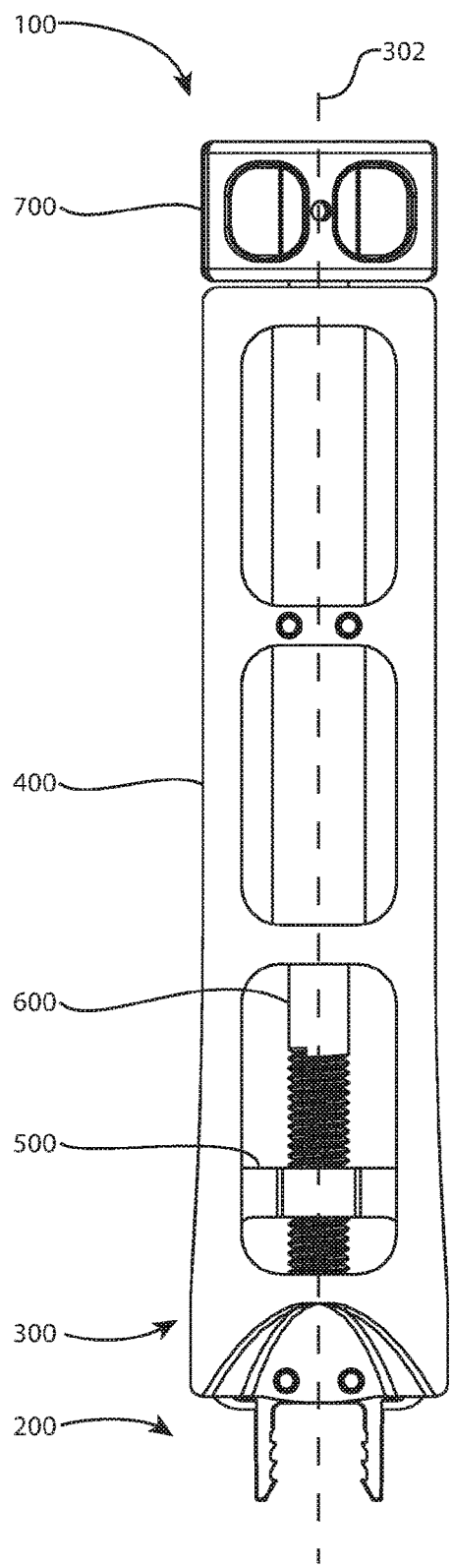
FIG. 7 is a front view of the system of FIG. 1 designed for a small size implant.
Figure 8:
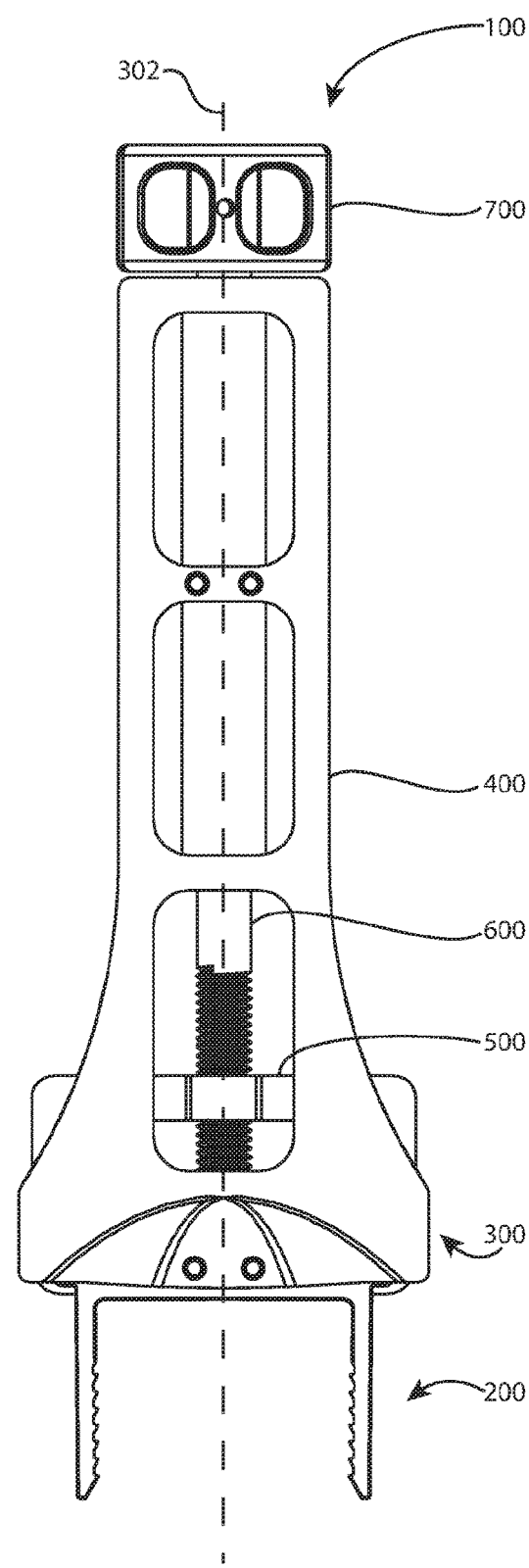
FIG. 8 is a front view of the system of FIG. 1 designed for a large size implant.

The illustrated inserter 300 may have a first plane of symmetry along plane 302 of FIG. 4, which is shown edge on and is thus represented by a line 302, and may have a second plane of symmetry along plane 304 of FIG. 3, which is shown edge on and is thus represented by section line 4-4. The first plane of symmetry divides the inserter 300 into identical left and right halves. The first plane of symmetry is also shown in FIGS. 7 and 8. The second plane of symmetry divides the inserter 300 into identical front and back halves. The first and second planes of symmetry are perpendicular to each other. The first and second planes of symmetry may also apply to the implant 200, the body 400, the jaw member 500, the drive shaft 600, and the knob 700. However, in other examples, the inserter 300 and/or implant 200 may have only one plane of symmetry, or no plane of symmetry so that they are asymmetric.

Figure 10:
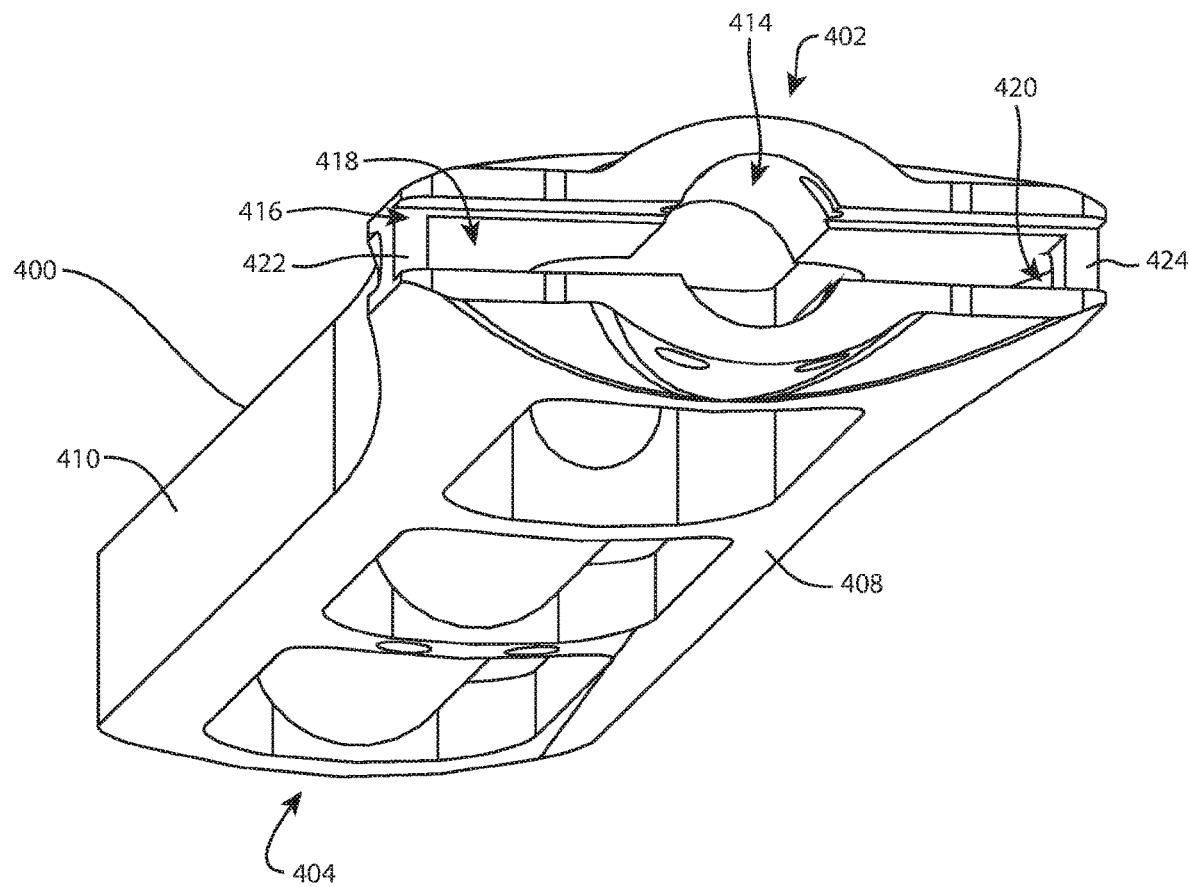
FIG. 10 is a perspective view of a body of the inserter of FIG. 1.

The body 400 is an elongated part that extends between a distal end 402 and an opposite proximal end 404. The distal end 402 may be referred to as a working portion and the proximal end 404 may be referred to as a handle. The body 400 has a front surface 406, an opposite back surface 408, a left side 410, and an opposite right side 412. A central longitudinal passageway 414 extends through the body 400 between the distal and proximal ends 402, 404. A groove 416 extends across a distal aspect of the distal end 402 from left to right and extends proximally into the body 400 to a first depth measured from the distal aspect. A pocket 418 extends from the groove 416 proximally into the body 400 to intersect a slot 420 that extends through the body 400 between the sides 410, 412 proximal to the groove 416. The slot 420 communicates with the groove 416 via the pocket 418 and is separated from the groove 416 by left and right columns 422, 424 which extend from front to back on either side of the pocket 418. The pocket 418 may be narrower, front to back, than the groove 416 so that the bottom of the groove 416 extends across the front and back sides of the pocket 418 as seen best in FIGS. 4 and 10. Left and right holes 426, 428 extend through the distal end 402 from front to back across the central longitudinal passageway 414. The slot 420 may intersect a window 430 that extends through the body 400 between the front and back surfaces 406, 408. The window 430 may extend proximally past the proximal end of the slot 420. Left and right holes 432, 434 extend through the body 400 proximal to the window 430 (if present) from front to back across the central longitudinal passageway 414.

The jaw member 500 includes a central body 502 with left and right arms 504, 506. The body 502 may be cylindrical and may include internal threads 508. Other examples may lack internal threads. The left arm 504 extends laterally from the body 502, bends distally at a left elbow 510, extends distally, and terminates in a left hook 512 that cups toward the right arm 506. The right arm 506 extends laterally from the body 502, bends distally at a right elbow 514, extends distally, and terminates in a right hook 516 that cups toward the left arm 504. The right arm 506 may optionally be a mirror image of the left arm 504, as shown in this example. The hooks 512, 516 may be replaced with other connection features that correspond to the particular connecting means of the implant 200, for example the hooks may be replaced with couplings that engage the front-to-back connecting means mentioned above.

The drive shaft 600 is an elongated cylindrical part with an externally threaded distal portion 602, a circumferential groove 604, and a proximal portion 606 with a transverse hole 608. The groove 604 is between the externally threaded distal portion 602 and the hole 608, in a middle portion of the drive shaft 600.

Figure 5:
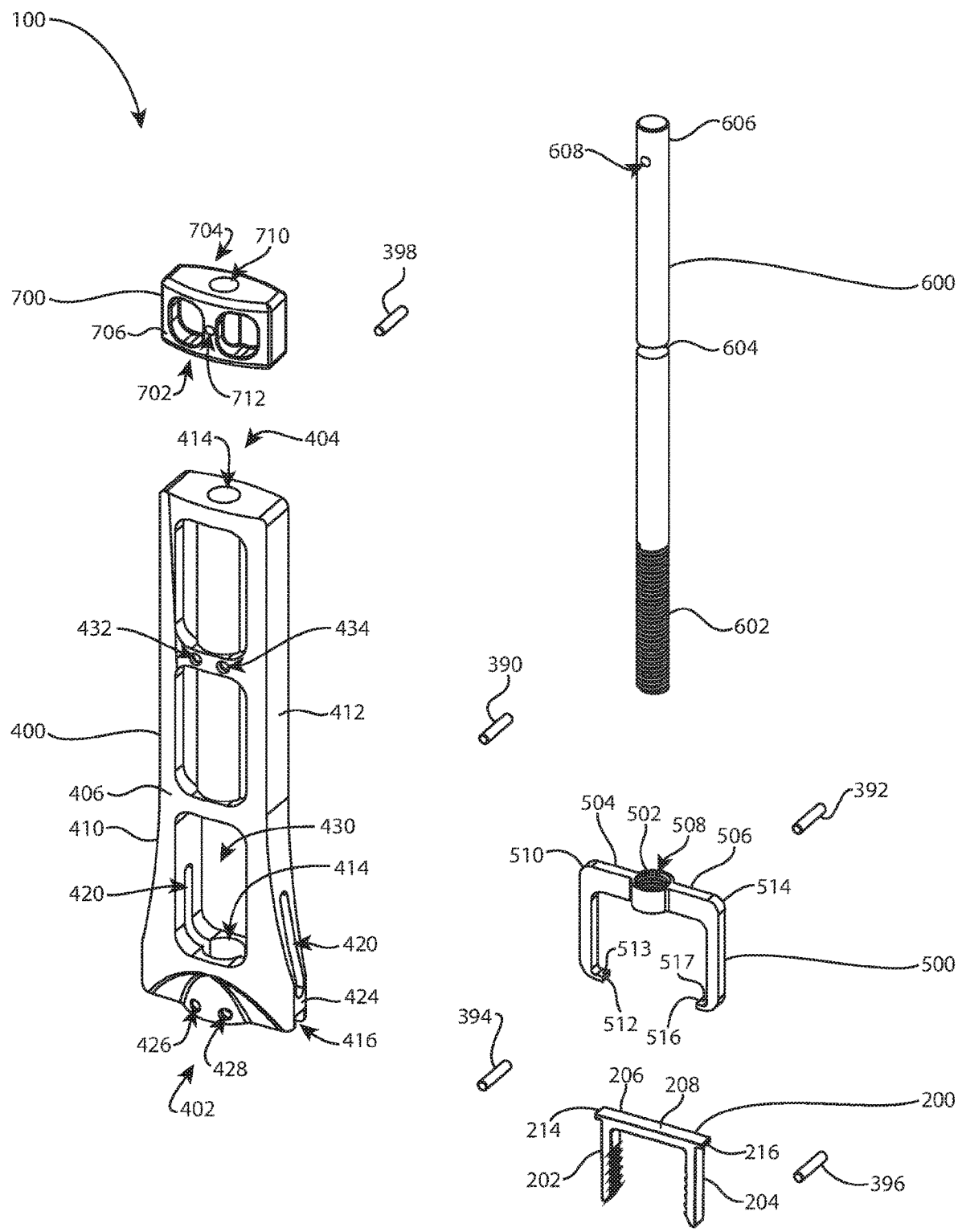
FIG. 5 is an exploded perspective view of the system of FIG. 1.
Figure 6:
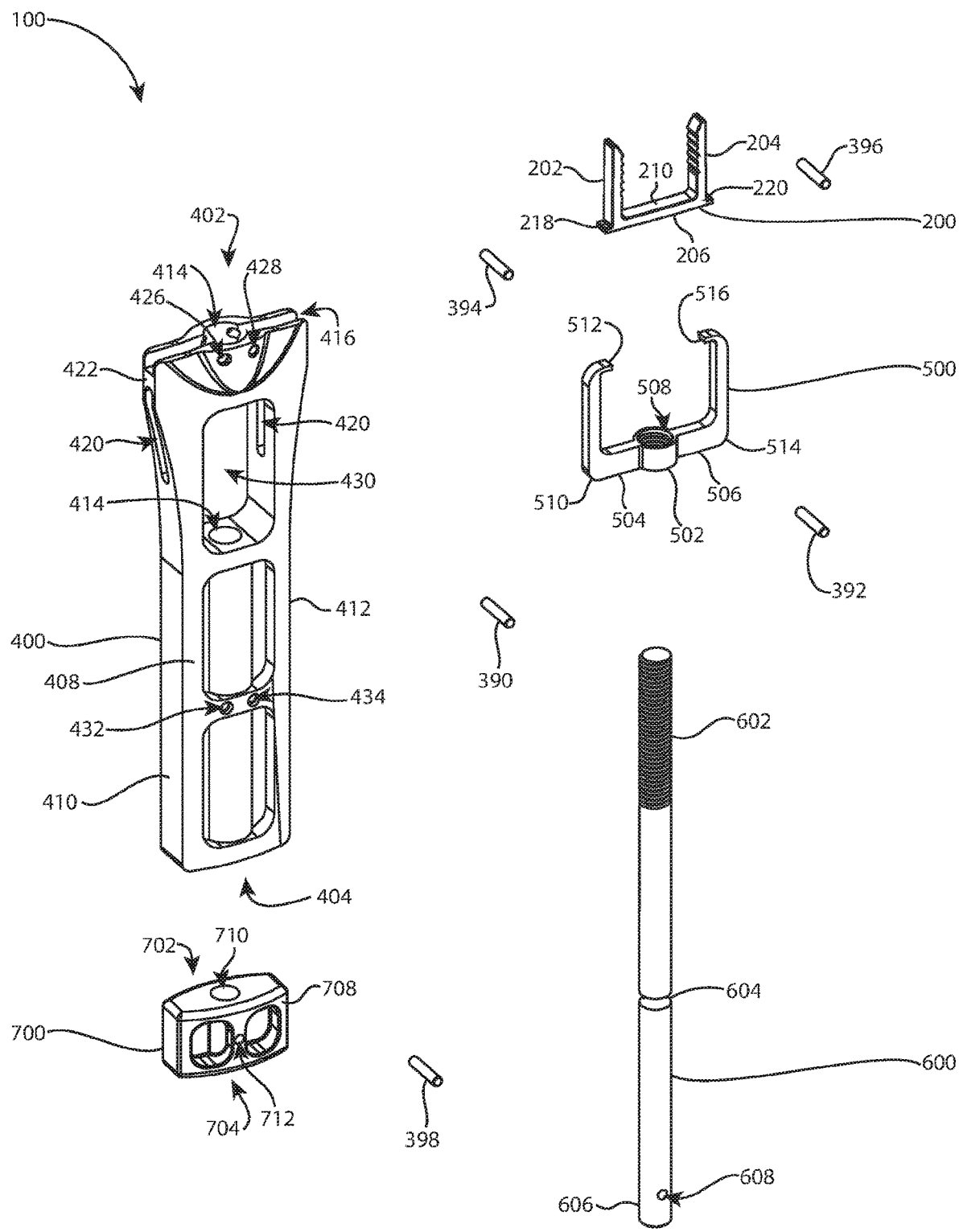
FIG. 6 is another exploded perspective view of the system of FIG. 1 from a different direction.

The knob 700 has a generally rectangular solid shape. However, the long sides of the rectangle may bow outwards to mimic the shape of the proximal end 404 of the body 400, as best seen in FIG. 5. The knob 700 extends between a distal end 702 and an opposite proximal end 704. The knob 700 has a front surface 706 and an opposite back surface 708. The front and back surfaces 706, 708 may bow outwardly to mimic the shape of the proximal end 404 of the body 400. A central longitudinal passageway 710 extends through the knob 700 between the distal and proximal ends 702, 704. An optional transverse hole 712 extends through the knob 700 between the front and back surfaces 706, 708.

When the inserter 300 is fully assembled (operatively assembled), the pocket 418 and slot 420 of the body 400 receive the jaw member 500. The jaw member 500 is oriented so that the body 502 is toward the proximal end 404, the arms 504, 506 are between the columns 422, 424, and the hooks 512, 516 are toward the distal end 402. The holes 426, 428 receive ram pins 394, 396. While two holes 426, 428 and two ram pins 394, 396 are shown, a single hole and ram pin may be used instead, preferably centrally located distal to the drive shaft 600. The ram pin(s) may be referred to as static support(s) against whose resistance the implant elastically deforms. In other examples, the ram pin(s) may be replaced by one or more static supports or ram features that are integrally formed with the body 400 or another component part of the inserter 300. The central longitudinal passageway of the body 400 receives the drive shaft 600. The drive shaft 600 is oriented so that the proximal portion 606 is toward the proximal end 404, the groove 604 is between the holes 432, 434, and the distal portion 602 is toward the distal end 402. The holes 432, 434 and the groove 604 receive drive shaft pins 390, 392. The internal threads 508 of the jaw member 500 thread onto the externally threaded distal portion 602. The central longitudinal passageway 710 of the knob 700 receives the proximal portion 606 of the drive shaft 600 with the holes 712, 608 aligned. The holes 712, 608 receive a knob pin 398. Alternatively, the knob 700 may be connected to the drive shaft 600 by overmolding instead of a cross pin.

A method of assembling the inserter 300 may include any or all of the following steps in any order: threading the jaw member 500 onto the drive shaft 600; inserting the drive shaft 600 in the central longitudinal passageway 414 of the body 400; inserting the jaw member 500 in the slot 420 of the body 400; coupling the knob 700 to the drive shaft 600; inserting the ram pins 394, 396 in the holes 426, 428; inserting the drive shaft pins 390, 392 in the holes 432, 434 and the groove 604; and inserting the knob pin 398 in the holes 712, 608.

When the inserter 300 is fully assembled, the drive shaft 600 and knob 700 are fixed together. The drive shaft 600 and knob 700 are free to rotate together relative to the body 400 and the jaw member 500. The drive shaft 600 and knob 700 are unable to translate proximal-distal relative to the body 400 due to the pins 390, 392 in the holes 432, 434 and the groove 604. Clockwise rotation of the drive shaft 600 causes the jaw member 500 to move proximally relative to the body 400; counterclockwise rotation of the drive shaft 600 causes the jaw member 500 to move distally relative to the body 400. The upper surface 208 of the bridge 206 of the implant 200 and the ram pins 394, 396 may remain in contact when the jaw member 500 moves proximally.

In the example shown, the arms 504, 506 of the jaw member 500 are static, meaning that the arms do not move relative to each other as the drive shaft 600 is rotated clockwise or counterclockwise. The static arms may be supported by the columns 422, 424 to prevent the arms from spreading apart laterally, for example when subjected to service loads during use.

In another example, the arms 504, 506 may be dynamic, meaning that the arms move relative to each other as the drive shaft 600 is rotated clockwise or counterclockwise. The dynamic arms 504, 506 may spread apart as the drive shaft 600 is rotated counterclockwise and the jaw member 500 moves distally relative to the body 400, and may close together as the drive shaft 600 is rotated clockwise and the jaw member 500 moves proximally. The dynamic arms 504, 506 may be squeezed together by the columns 422, 424 as the jaw member moves proximally. The dynamic arms 504, 506 in this example may be designed with geometry that enhances their elastic deflection, and the jaw member 500 may be made from a suitably elastic material.

When the implant 200 and the inserter 300 are fully assembled (operatively assembled), the groove 416 receives a proximal portion of the bridge 206, the ram pins 394, 396 may be adjacent to or may contact the upper surface 208, the hooks 512, 516 engage under the connecting means 214, 216, and the bone engaging members 202, 204 extend distally from the inserter 300. Proximal surfaces 513, 517 of the hooks 512, 516 may engage the lower surfaces 218, 220 of the connecting means 214, 216. The implant 200 and the inserter 300 may be fully assembled with the implant 200 in the free state; the four points of contact (ram pins 394, 396 and hooks 512, 516) acting on the bridge 206 and connecting means 214, 216 may exert loads that are below the threshold for elastic or plastic deflection or deformation of the implant 200. The inserter 300 supports and constrains the implant 200 from the front and back, left and right, and top and bottom (lower surfaces 218, 220). Referring to FIGS. 2 and 4, the entire inserter 300 is proximal to the lower surface 210 of the bridge 206. In particular, the dashed extension lines 210' and 210" in FIG. 4 show the level of the lower surface 210 versus the hooks 512, 516. This is significant because the lower surface 210 rests against a bone surface when the implant 200 is implanted. The implant 200 may be fully seated against the bone surface without interference from the hooks 512, 516. Similarly, there is no interference from the front or back distal aspects of the body 400 (FIG. 2).

A method of assembling the implant 200 and the inserter 300 may include any or all of the following steps in any order: rotating the knob 700 counterclockwise; rotating the drive shaft 600 counterclockwise; moving the jaw member 500 distally relative to the body 400; extending the hooks 512, 516 distally from the distal end 402 of the body 400, preferably far enough to provide clearance for the bridge 206 of the implant 200 distal to the body 400; aligning the bridge 206 of the implant 200 parallel to the groove 416; sliding the hooks 512, 516 under the connecting means 214, 216 from the front or back; rotating the knob 700 clockwise; rotating the drive shaft 600 clockwise; moving the jaw member 500 proximally relative to the body 400; moving the bridge 206 into the groove 416; and contacting the bridge 206 with the ram pins 394, 396. Alternatively, the bridge 206 may be aligned transverse to the groove 416 and the implant 200 rotated relative to the inserter 300 so that the connecting means 214, 216 rotate into engagement with the hooks 512, 516.

Another method of assembling the implant 200 and the inserter 300 may include any or all of the following steps in any order: rotating the knob 700 counterclockwise; rotating the drive shaft 600 counterclockwise; moving the jaw member 500 distally relative to the body 400; extending the hooks 512, 516 distally from the distal end 402 of the body 400, preferably far enough to provide clearance for the bridge 206 of the implant 200 distal to the body 400; spreading the hooks 512, 516 apart; aligning the bridge 206 of the implant 200 parallel to the groove 416; sliding the connecting means 214, 216 between the hooks 512, 516 from distal to proximal; rotating the knob 700 clockwise; rotating the drive shaft 600 clockwise; moving the jaw member 500 proximally relative to the body 400; closing the hooks 512, 516 together under the connecting means 214, 216; and contacting the bridge 206 with the ram pins 394, 396.

The inserter 300 may be disconnected from the implant 200 at least by reversing the assembly steps.

When the implant 200 and the inserter 300 are operatively assembled, the inserter 300 may be actuated to move the implant 200 between the free state and an elastically deformed state. Referring to FIG. 4, clockwise rotation of the knob 700 and the drive shaft 600 causes the jaw member 500 to move proximally relative to the body 400, causing the hooks 512, 516 to pull proximally on the connecting means 214, 216 against the static resistance or support of the ram pins 394, 396 or other static support feature(s). This causes the bridge 206 to elastically deform in three or four point bending, which causes the bone engaging members 202, 204 to spread apart. Counterclockwise rotation of the knob 700 and the drive shaft 600 causes the jaw member 500 to move distally relative to the body 400, reducing the proximal force of the hooks 512, 516 on the connecting means 214, 216. This allows the implant 200 to relax toward the free state.

A surgical method for stabilizing first and second bone fragments may include any or all of the following steps in any order: assembling the inserter 300; assembling the implant 200 and the inserter 200; actuating the inserter 200; moving the jaw member 500 proximally relative to the body 400; moving the implant 200 from the free state to an elastically deformed state; moving the bone engaging members 202, 204 from a distally-converging state to a parallel state; creating a first hole in a first bone fragment; creating a second hole in a second bone fragment; inserting the left bone engaging member 202 in the first hole; inserting the right bone engaging member 204 in the second hole; seating the lower surface 210 against a surface of the first or second bone fragment; releasing the inserter 300; moving the jaw member 500 distally relative to the body 400; moving the implant 200 from the elastically deformed state toward the free state; moving the bone engaging members 202, 204 from a parallel state toward a distally-converging state; and disconnecting the inserter 300 from the implant 200.

Figure 11:
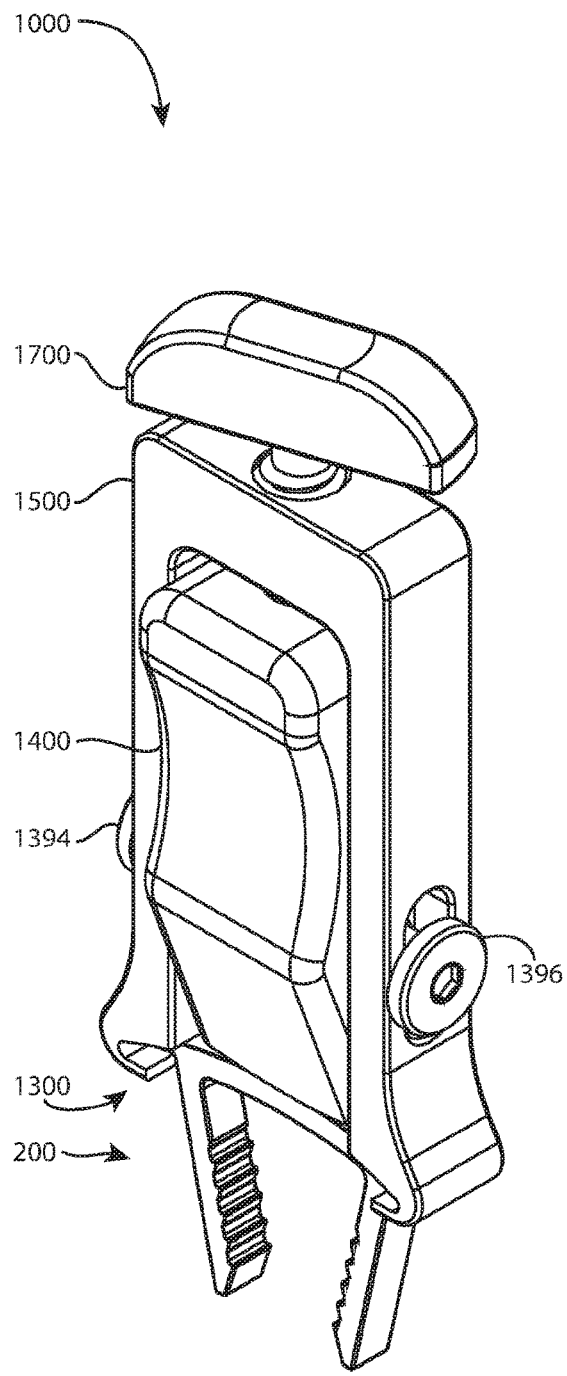
FIG. 11 is a perspective view of another system with the implant of FIG. 1 coupled to another inserter.
Figure 12:
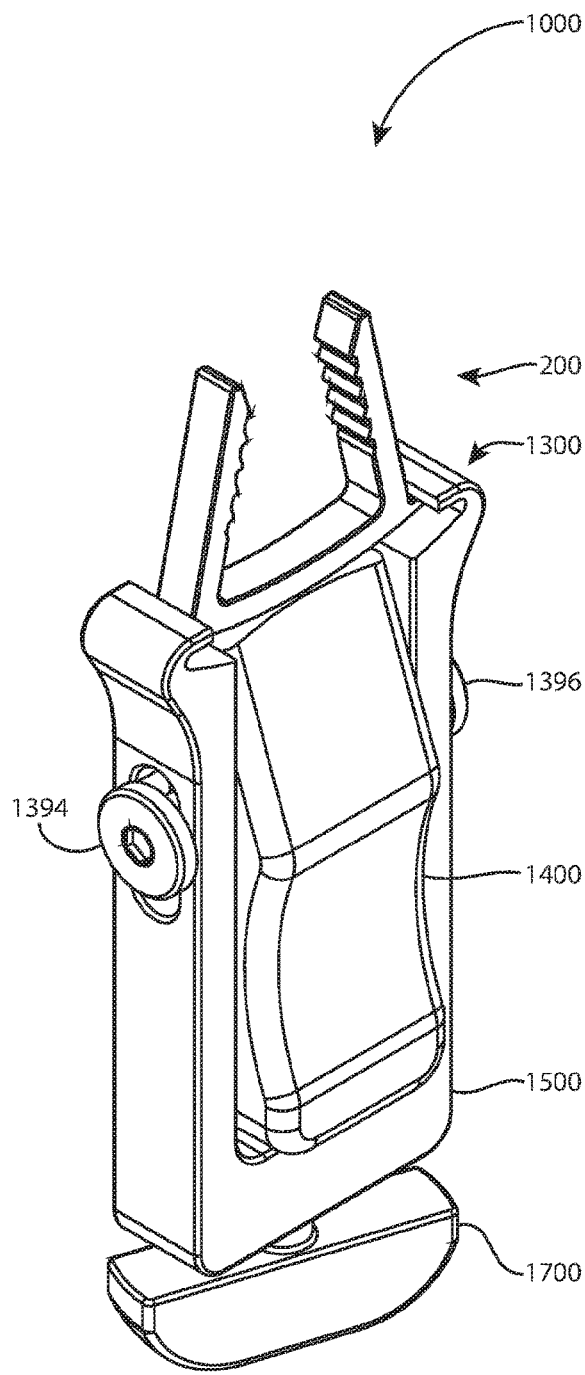
FIG. 12 is another perspective view of the system of FIG. 11 from a different direction.

Referring to FIGS. 11 and 12, another implant delivery system 1000 includes the implant 200 and another inserter 1300. FIG. 17 illustrates the system 1000 with the implant 200 coupled to the inserter 1300, the implant 200 in a free state. FIG. 18 illustrates the system 1000 with the implant 200 coupled to the inserter 1300, the implant 200 in an elastically deformed state.

Referring to FIGS. 11-18, the inserter 1300 may include a body 1400, a jaw member 1500, a knob 1700, a left screw 1394, a right screw 1396, a front pin 1390, and a rear pin 1392.

Figure 13:
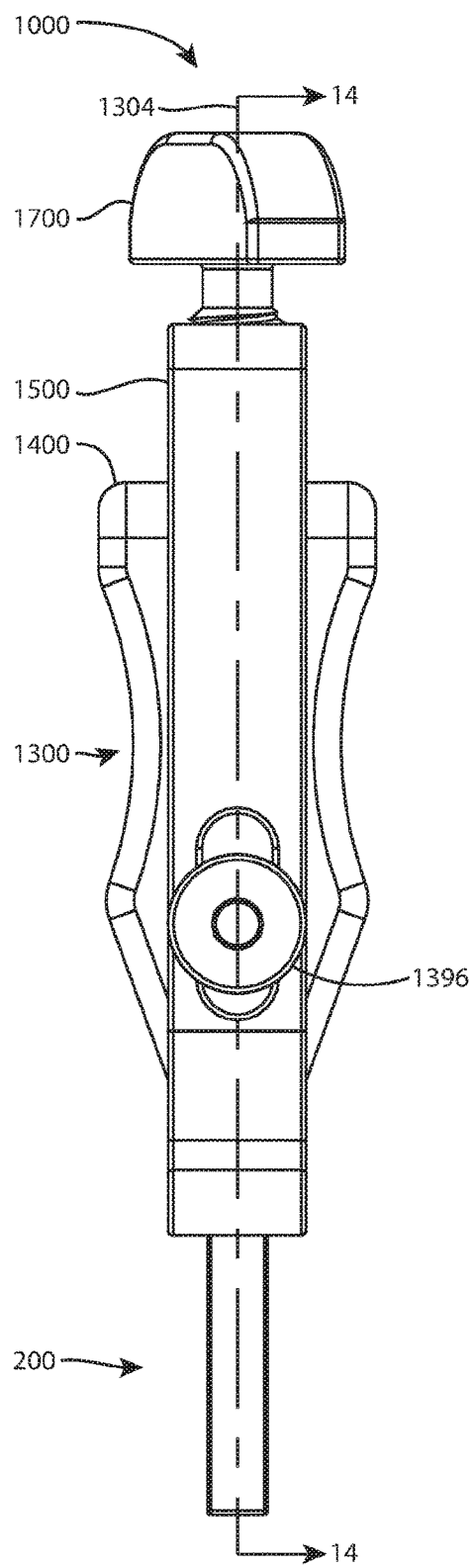
FIG. 13 is a side view of the system of FIG. 11.
Figure 14:
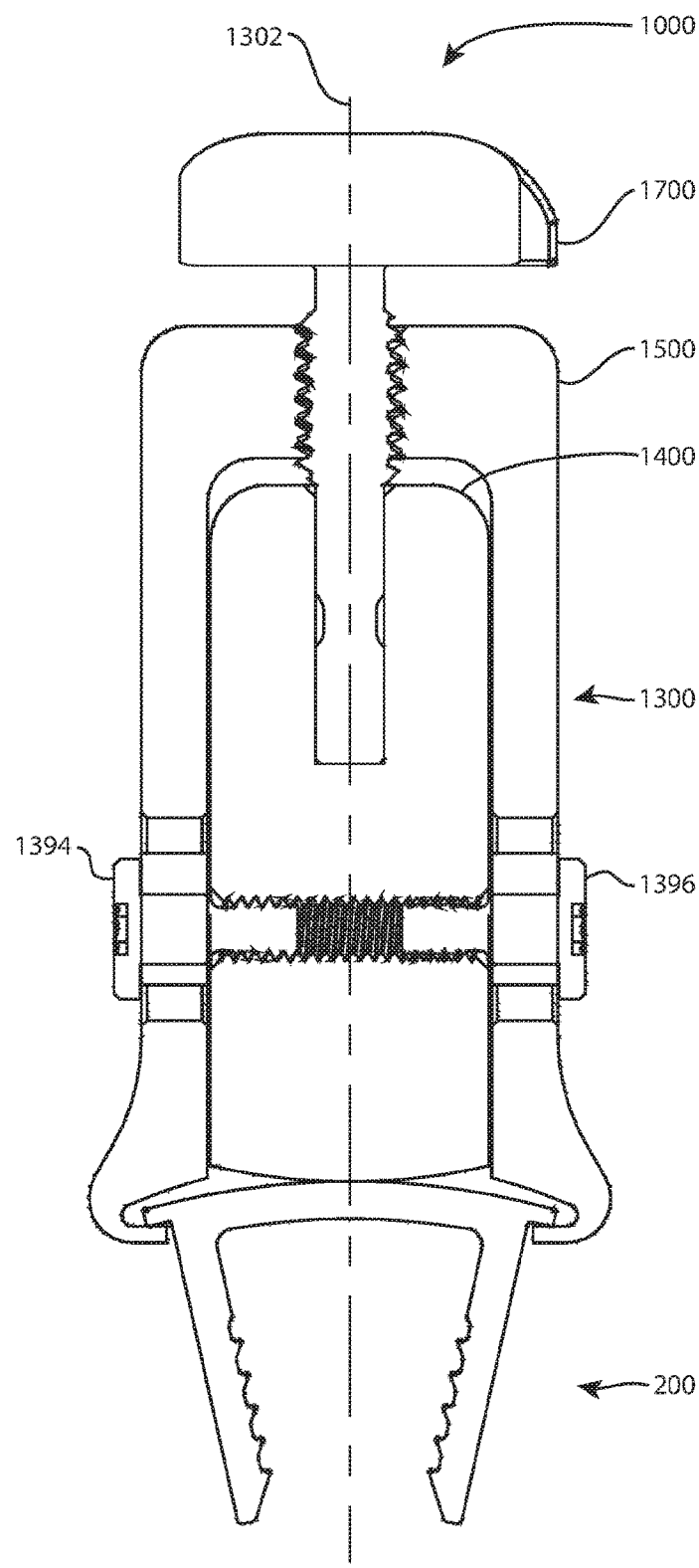
FIG. 14 is a cross sectional view of the system of FIG. 11, taken along section line 14-14 of FIG. 13.
Figure 15:
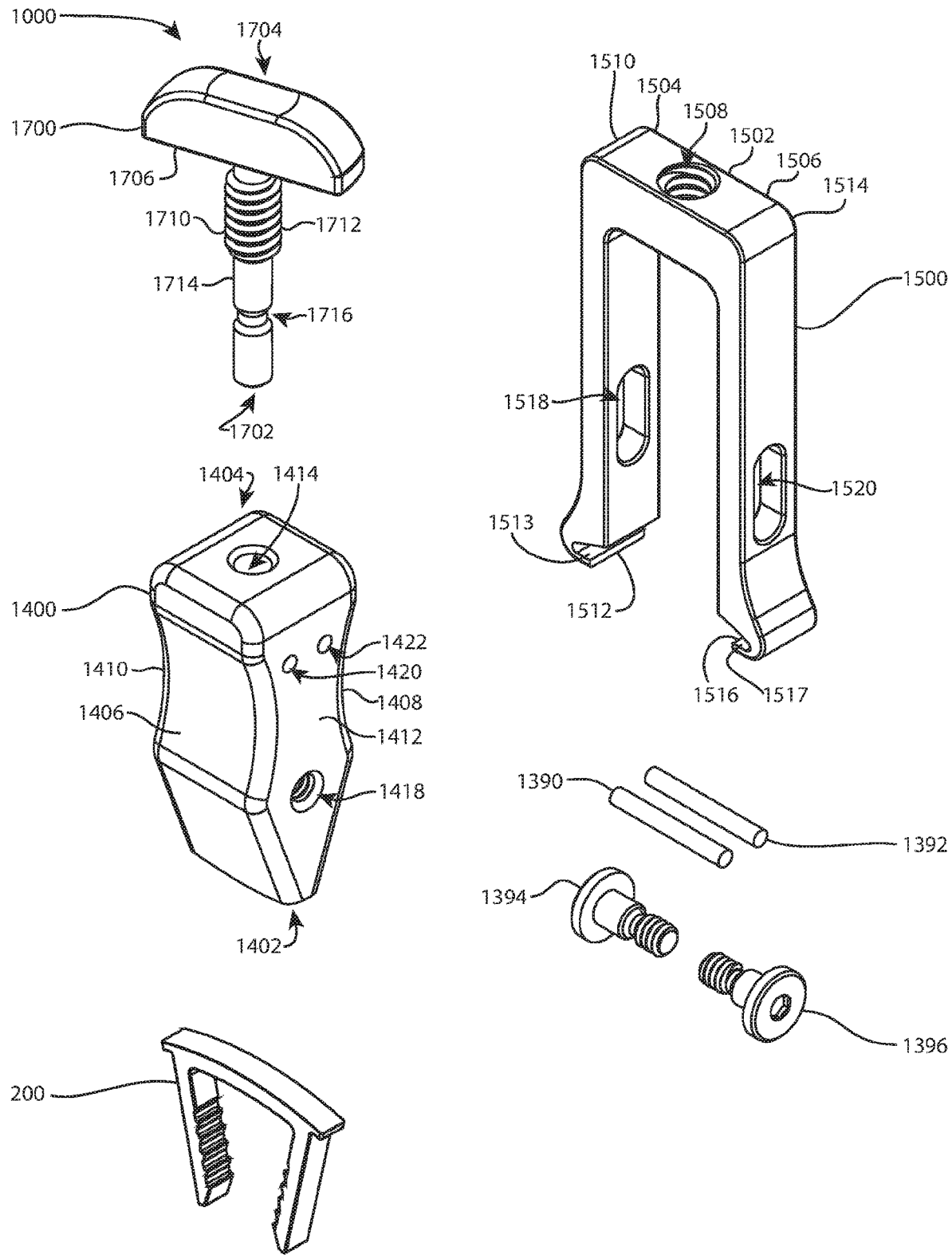
FIG. 15 is an exploded perspective view of the system of FIG. 11.
Figure 16:
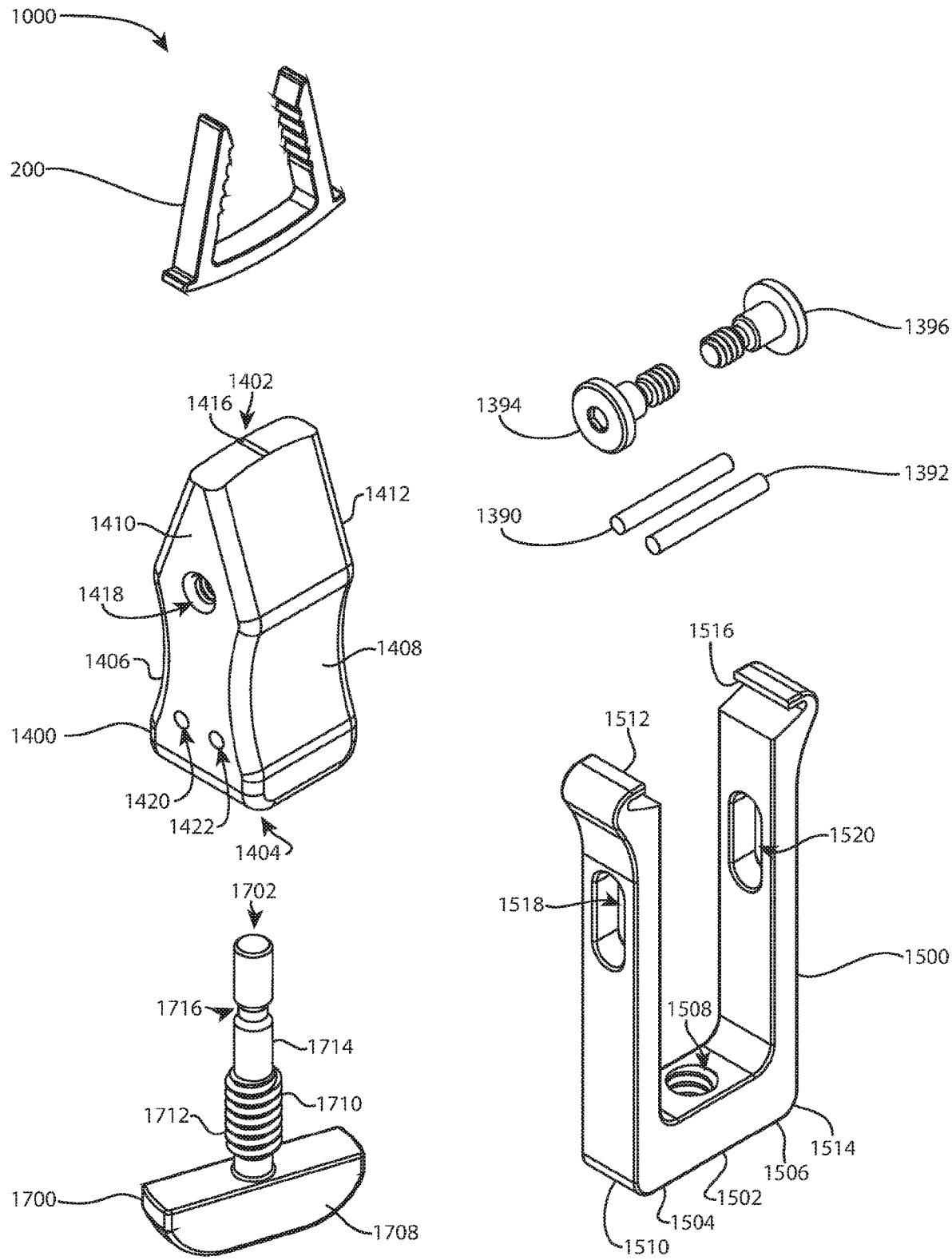
FIG. 16 is another exploded perspective view of the system of FIG. 11 from a different direction.

The illustrated inserter 1300 may have a first plane of symmetry along plane 1302 of FIG. 14, which is shown edge on and is thus represented by a line 1302, and may have a second plane of symmetry along plane 1304 of FIG. 13, which is shown edge on and is thus represented by section line 14-14. The first plane of symmetry divides the inserter 1300 into identical left and right halves. The first plane of symmetry is also shown in FIGS. 17 and 18. The second plane of symmetry divides the inserter 1300 into identical front and back halves. The first and second planes of symmetry are perpendicular to each other. The first and second planes of symmetry may also apply to the implant 200, the body 1400, the jaw member 1500, and the knob 1700. However, in other examples, the inserter 1300 and/or implant 200 may have only one plane of symmetry, or no plane of symmetry so that they are asymmetric.

The body 1400 is an elongated part that extends between a distal end 1402 and an opposite proximal end 1404. The distal end 1402 may be referred to as a working portion. The body 1400 has a front surface 1406, an opposite back surface 1408, a left side 1410, and an opposite right side 1412. A central longitudinal hole 1414 extends into the body 1400 from the proximal end 1404. A distal aspect 1416 of the distal end 1402 may be convex in the front or back view, as seen in FIGS. 14, 17, and 18, and may be straight in the side view. A threaded hole 1418 extends through the body 1400 between the left and right sides 1410, 1412 proximal to the distal aspect 1416. Front and rear holes 1420, 1422 extend through the body 1400 between the left and right sides 1410, 1412 proximal to the threaded hole 1418. The holes 1420, 1422 intersect the front and rear sides, respectively, of the central longitudinal hole 1414.

The jaw member 1500 includes a central body 1502 with left and right arms 1504, 1506. The body 1502 in this example may be rectangular, may be continuous with the arms 1504, 1506, and may include central longitudinal internal threads 1508. Other examples may lack internal threads. The left arm 1504 extends laterally from the body 1502, bends distally at a left elbow 1510, extends distally, and terminates in a left hook 1512 that cups toward the right arm 1506. The right arm 1506 extends laterally from the body 1502, bends distally at a right elbow 1514, extends distally, and terminates in a right hook 1516 that cups toward the left arm 1504. The right arm 1506 may optionally be a mirror image of the left arm 1504, as shown in this example. The hooks 1512, 1516 may be replaced with other connection features that correspond to the particular connecting means of the implant 200, for example the hooks may be replaced with couplings that engage the front-to-back connecting means mentioned above. A longitudinal slot 1518 may extend through the left arm 1504 from left to right and another longitudinal slot 1520 may extend through the right arm 1506 from left to right. The slots 1518, 1520 may be aligned to form a single slot extending from left to right through the jaw member 1500 proximal to the hooks 1512, 1516 and distal to the elbows 1510, 1514.

The knob 1700 extends between a distal end 1702 and an opposite proximal end 1704. The knob 1700 has a front surface 1706 and an opposite back surface 1708. The distal end 1702 includes a distally-extending shaft 1710 with a proximal externally threaded portion 1712 and a distal smooth portion 1714. A circumferential groove 1716 extends around the smooth portion 1714 about halfway along its proximal-distal length. The externally threaded portion 1712 threadedly engages the internal threads 1508 of the jaw member 1500. The proximal end 1704 is laterally enlarged relative to the shaft 1710, forming a T-handle.

When the inserter 1300 is fully assembled (operatively assembled), the body 1400 is received between the left and right arms 1504, 1506 of the jaw member 1500. The proximal end 1404 faces the central body 1502 and the distal end 1402 is near the hooks 1512, 1516. The shaft 1710 of the knob 1700 extends distally through the internal threads 1508 of the jaw member 1500 and into the central longitudinal hole 1414 of the body. The externally threaded portion 1712 of the shaft 1710 threads into engagement with the internal threads 1508 and the smooth portion 1714 is received in the hole 1414. The circumferential groove 1716 is aligned with the holes 1420, 1422, and the pins 1390, 1392 are received in the holes 1420, 1422, respectively, and in the groove 1716 to couple the knob 1700 to the body 1400 in a fixed axial (proximal-distal) relationship, while leaving the knob free to rotate relative to the body. Optionally, the left and/or right arms 1504, 1506 may include access windows (not shown) that align with the holes 1420, 1422 so that the pins 1390, 1392 can be inserted in the holes 1420, 1422. Optionally, the pins 1390, 1392 and holes 1420, 1422 may be oriented front-to-back instead of left-to-right as shown. The left screw 1394 extends through the slot 1518 and threads into the hole 1418 from the left. The right 1396 extends through the slot 1520 and threads into the hole 1418 from the right.

A method of assembling the inserter 1300 may include any or all of the following steps in any order: inserting the body 1400 between the left and right arms 1504, 1506 of the jaw member 1500; inserting the shaft 1710 of the knob 1700 through the internal threads 1508 of the jaw member and into the central longitudinal hole 1414 of the body; threading the externally threaded portion 1712 of the shaft into engagement with the internal threads 1508; positioning the circumferential groove 1716 adjacent to the holes 1420, 1422 of the body; inserting the pins 1390, 1396 into the holes 1420, 1422, respectively, and in the groove 1716; inserting the left screw 1394 through the slot 1518 of the jaw member and threading the left screw 1394 into the threaded hole 1418 of the body; and inserting the right screw 1396 through the slot 1520 and threading the right screw 1396 into the threaded hole 1418.

When the inserter 1300 is fully assembled, the knob 1700 is unable to translate proximal-distal relative to the body 1400 due to the pins 1390, 1392 in the holes 1420, 1422. However, the knob 1700 is free to rotate about the central longitudinal axis of the shaft 1710 relative to the body 1400. The knob 1700 is in threaded engagement with the jaw member 1500 and is therefore able to rotate and simultaneously move proximal-distal relative to the jaw member. Clockwise rotation of the knob 1700 causes the jaw member 1500 to move proximally relative to the body 1400; counterclockwise rotation of the knob causes the jaw member to move distally relative to the body. The distal aspect 1416 of the body 1400 and the upper surface 208 of the bridge 206 of the implant 200 may remain in contact when the jaw member 500 moves proximally.

When the implant 200 and the inserter 1300 are fully assembled (operatively assembled), the distal aspect 1416 of the body 1400 may be adjacent to, or may contact, the upper surface 208 of the bridge 206, the hooks 1512, 1516 engage under the connecting means 214, 216, and the bone engaging members 202, 204 extend distally from the inserter 200. Proximal surfaces 1513, 1517 of the hooks 1512, 1516 may engage the lower surfaces 218, 220 of the connecting means 214, 216. The implant 200 and the inserter 1300 may be fully assembled with the implant 200 in the free state; the three points of contact (distal aspect 1416 and hooks 1512, 1516) acting on the bridge 206 and connecting means 214, 216 may exert loads that are below the threshold for elastic or plastic deflection or deformation of the implant 200. The inserter 1300 supports and constrains the implant 200 from the left and right, and top and bottom (lower surfaces 218, 220). Referring to FIGS. 12 and 14, the entire inserter 1300 is proximal to the lower surface 210 of the bridge 206.

A method of assembling the implant 200 and the inserter 1300 may include any or all of the following steps in any order: rotating the knob 1700 counterclockwise; moving the jaw member 1500 distally relative to the body 1400; extending the hooks 1512, 1516 distally beyond the distal end 1402 of the body 1400, preferably far enough to provide clearance for the bridge 206 of the implant 200 distal to the body 1400; aligning the bridge 206 of the implant 200 parallel to the distal aspect 1416; sliding the hooks 1512, 1516 under the connecting means 214, 216 from the front or back; rotating the knob 1700 clockwise; moving the jaw member 1500 proximally relative to the body 1400; and contacting the bridge 206 with the distal aspect 1416. Alternatively, the bridge 206 may be aligned transverse to the distal aspect 1416 and the implant 200 rotated relative to the inserter 1300 so that the connecting means 214, 216 rotate into engagement with the hooks 1512, 1516.

The inserter 1300 may be disconnected from the implant 200 at least by reversing the assembly steps.

When the implant 200 and the inserter 1300 are operatively assembled, the inserter 1300 may be actuated to move the implant 200 between the free state and an elastically deformed state. Referring to FIG. 14, clockwise rotation of the knob 1700 causes the jaw member 1500 to move proximally relative to the body 1400, causing the hooks 1512, 1516 to pull proximally on the connecting means 214, 216 against the static resistance or support of the distal aspect 1416 or other static support feature(s). This causes the bridge 206 to elastically deform in three point bending, which causes the bone engaging members 202, 204 to spread apart. Counterclockwise rotation of the knob 1700 causes the jaw member 1500 to move distally relative to the body 1400, reducing the proximal force of the hooks 1512, 1516 on the connecting means 214, 216. This allows the implant 200 to relax toward the free state.

A surgical method for stabilizing first and second bone fragments may include any or all of the following steps in any order: assembling the inserter 1300; assembling the implant 200 and the inserter 200; actuating the inserter 200; moving the jaw member 1500 proximally relative to the body 1400; moving the implant 200 from the free state to an elastically deformed state; moving the bone engaging members 202, 204 from a distally-converging state to a parallel state; creating a first hole in a first bone fragment; creating a second hole in a second bone fragment; inserting the left bone engaging member 202 in the first hole; inserting the right bone engaging member 204 in the second hole; seating the lower surface 210 against a surface of the first or second bone fragment; releasing the inserter 1300; moving the jaw member 1500 distally relative to the body 1400; moving the implant 200 from the elastically deformed state toward the free state; moving the bone engaging members 202, 204 from a parallel state toward a distally-converging state; and disconnecting the inserter 1300 from the implant 200.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An implant delivery system comprising:
   an implant comprising a body, a first bone engagement member, a second bone engagement member, a first connecting means, and a second connecting means, wherein the body extends between a first end and an opposite second end to establish a longitudinal direction of the body, wherein the first bone engagement member extends from the first end along a transverse direction that is transverse to the longitudinal direction, wherein the second bone engagement member extends from the second end along the transverse direction beside the first bone engagement member along the longitudinal direction, wherein the first connecting means extends outwardly from the first end along the longitudinal direction such that a first outer perimeter of the first connecting means extends from the body to the first bone engagement member, wherein the second connecting means extends outwardly from the second end along the longitudinal direction such that a second outer perimeter of the second connecting means extends from the body to the second bone engagement member, wherein the implant comprises an implant free state in which the first and second bone engagement members converge as they extend from the body, and an elastically deformed state in which the first and second bone engagement members are spread apart relative to the implant free state; and
   an inserter removably connectable to the implant, the inserter comprising a body, a first and arm that extends from the body and terminates at a first hook, a second arm that extends from the body and terminates at a second hook such that the first and second hooks are not movable relative to each other, and the inserter further including a support;
   wherein when the inserter is connected to the implant, the first hook is configured to contact the first outer perimeter of the first connecting means and the second hook is configured to contact the second outer perimeter of the second connecting means, wherein the inserter is configured to cause relative linear translation along the transverse direction between the support and the first and second hooks to cause the body to elastically deform, thereby moving the implant from the implant free state to the elastically deformed state, and
   wherein the implant defines a length from a longitudinally outermost end of the first connecting means to a longitudinally outermost end of the second connecting means that is greater than each of 1) a thickness of the body along the transverse direction and 2) a width of the body along a direction that is perpendicular to each of the longitudinal direction and the transverse direction.

2. The implant delivery system of claim 1, wherein the inserter comprises a body and a jaw member that receives the body, wherein the jaw member defines the left and right hooks, and a distal end of the body defines the support.

3. The implant delivery system of claim 1, wherein the inserter comprises a body and a jaw member that is received in the body, wherein the jaw member defines the left and right hooks, and the body supports a ram pin that defines the support.

4. The implant delivery system of claim 1, wherein the first and second hooks face each other.

5. The implant delivery system of claim 1, wherein the width of the body is defined from a first side to a second side, and each of the first and second sides extends straight and linearly.

6. The implant delivery system of claim 1, wherein the inserter is configured to move the first and second hooks proximally with respect to the support so as to move the implant from the implant free state to the elastically deformed state.

7. An implant delivery system comprising:
   an implant comprising a body that defines a proximal surface and a distal surface opposite the proximal surface in a distal direction, wherein the implant body extends between a first end and a second end opposite the first end along a longitudinal direction, the implant further comprising a first bone engagement member that extends from the first end transverse to the body in the distal direction, and a second bone engagement member that is adjacent the first bone engagement member along the longitudinal direction and extends from the second end transverse to the body in the distal direction, the implant further defining a first distal surface that extends from the first end of the body along the longitudinal direction, and a second distal surface that extends from the second end of the body along the longitudinal direction, wherein the implant is movable between an implant free state in which the first and second bone engagement members converge as they extend from the body, and an elastically deformed state in which the first and second bone engagement members are spread apart relative to the implant free state; and an inserter that is removably connectable to the implant such that a support of the inserter engages against the proximal surface of the body, the inserter including a drive shaft, a body that threadedly receives the drive shaft, and first and second arms that extend from the body and define first and second hooks, respectively, that are configured to engage the first and second distal surfaces, respectively, of the implant, wherein when the inserter is connected to the implant, rotation of the drive shaft is configured to cause relative linear translation of the support and the first and second hooks along a transverse direction that is defined by the distal direction and a proximal direction opposite the distal direction, which in turn causes the implant to elastically deform from the implant free state to the elastically deformed state, wherein longitudinally outermost ends of the first and second distal surfaces are spaced from each other a longitudinal distance along the longitudinal direction that, the longitudinal distance is greater than a thickness of the body along the distal direction from the proximal surface to the distal surface, and the longitudinal distance is greater than a width of the body along a direction that is perpendicular to each of the longitudinal direction and the distal direction.

8. The implant delivery system of claim 7, wherein the implant comprises a first connection feature that extends outwardly from the first end along the longitudinal direction and defines the first distal surface, and a second connection feature that extends outwardly from the second end along the longitudinal direction and defines the second distal surface.

9. The implant delivery system of claim 8, wherein the inserter comprises a third connection feature that defines the first hook, a fourth connection feature that defines the second hook, the support is a static support, whereby when the inserter is connected to the implant, the first connection feature engages the third connection feature, the second connection feature engages the fourth connection feature, the implant body proximal surface faces the static support, and the entire inserter is proximal to the implant body distal surface, and wherein the instrument is configured to selectively translate the third and fourth connection features proximally and distally relative to the static support.

10. The implant delivery system of claim 9, wherein the first and second fixation members extend from the implant body distal surface.

11. The implant delivery system of claim 9, wherein the first and second connection features are lateral to the first and second fixation members.

12. The implant delivery system of claim 9, wherein when the inserter is connected to the implant, the first distal surface of the first connection feature engages a proximal surface of the third connection feature, and the second distal surface of the second connection feature engages a proximal surface of the fourth connection feature.

13. The implant delivery system of claim 9, wherein moving the third and fourth connection features proximally relative to the static support causes the implant body to elastically deform against the static support to move the implant into the elastically deformed state.

14. The implant delivery system of claim 9, wherein the inserter comprises a distal groove, wherein when the inserter is connected to the implant, a proximal portion of the implant body is received in the distal groove.

15. The implant delivery system of claim 14, wherein the static support is located within the distal groove.

16. The implant delivery system of claim 9, wherein the static support remains in contact with the implant body proximal surface at all times while the inserter is connected to the implant.

17. The implant delivery system of claim 9, wherein moving the third and fourth connection features distally relative to the static support when the implant is in the elastically deformed state causes the implant body to return to the implant free state.

18. The implant delivery system of claim 9, wherein the inserter comprises a body and a jaw member that receives the body, wherein the jaw member defines the left and right hooks, and a distal end of the body defines the static support.

19. The implant delivery system of claim 9, wherein the inserter comprises a body and a jaw member that is received in the body, wherein the jaw member defines the left and right hooks, and the body supports a ram pin that defines the static support.

20. The implant delivery system of claim 7, further comprising first and second extensions that project out with respect to the body, the first extension defining a first outer perimeter that extends from the body to the first bone engagement member, and the second extension defining a second outer perimeter that extends from the body to the second bone engagement member, wherein the first outer perimeter defines the first distal surface, and the second outer perimeter defines the second distal surface.

* * * * *